(12) United States Patent
Shi et al.

(10) Patent No.: US 11,180,544 B2
(45) Date of Patent: Nov. 23, 2021

(54) METHOD OF PRODUCING ANTIBODY FRAGMENT

(71) Applicant: City University of Hong Kong, Kowloon (HK)

(72) Inventors: Jiahai Shi, Kowloon (HK); Lai Leo Chan, Kowloon (HK); Likun Wei, Kowloon (HK); Limin Feng, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/805,507

(22) Filed: Nov. 7, 2017

(65) Prior Publication Data

US 2019/0135904 A1 May 9, 2019

(51) Int. Cl.
| | | |
|---|---|---|
| *C07K 16/00* | (2006.01) | |
| *C07K 16/18* | (2006.01) | |
| *C07K 16/40* | (2006.01) | |
| *C12Q 1/00* | (2006.01) | |
| *C07K 16/28* | (2006.01) | |

(52) U.S. Cl.
CPC .............. *C07K 16/18* (2013.01); *C07K 16/00* (2013.01); *C07K 16/28* (2013.01); *C07K 16/40* (2013.01); *C12Q 1/00* (2013.01); *C07K 2317/14* (2013.01); *C07K 2317/20* (2013.01); *C07K 2317/24* (2013.01); *C07K 2317/50* (2013.01); *C07K 2317/569* (2013.01); *C07K 2317/92* (2013.01)

(58) Field of Classification Search
CPC ........ C07K 16/18; C07K 16/00; C07K 16/28; C07K 16/40; C07K 2317/14; C07K 2317/20; C07K 2317/24; C07K 2317/50; C07K 2317/569; C07K 2317/92; C12Q 1/00
See application file for complete search history.

(56) References Cited

U.S. PATENT DOCUMENTS

| 7,977,071 B2* | 7/2011 | Nuttal | A61P 43/00 |
| | | | 435/69.6 |
| 2004/0106118 A1* | 6/2004 | Kolmar | C07K 14/245 |
| | | | 435/6.11 |
| 2010/0061989 A1* | 3/2010 | Jane | C12N 15/1137 |
| | | | 514/1.1 |
| 2016/0068600 A1* | 3/2016 | Barelle | C07K 16/005 |
| | | | 424/9.1 |

FOREIGN PATENT DOCUMENTS

| MX | 2015007459 A | * | 12/2016 | .......... C12N 5/0634 |
| WO | WO-2010033913 A1 | * | 3/2010 | ............. C07K 16/00 |

OTHER PUBLICATIONS

De Silva et al in "Determination of immunoglobulin novel antigen receptor (IgNAR) in vivo affinity maturation in brownbanded bamboo shark (Chiloscyllium punctatum)" The JSFS 85th Anniversary-Commemorative International Symposium "Fisheries Science for Future Generations" Meeting pub Sep. 22, 2017. (Year: 2017).*
Score report result for Bhatt & Zhang WO2010/033913. (Year: 2011).*
Score result for instant SEQ ID No. 6 to MX-2015007459-A published Dec. 6, 2016. (Year: 2016).*

* cited by examiner

*Primary Examiner* — Catherine S Hibbert
(74) *Attorney, Agent, or Firm* — Renner Kenner Greive Bobak Taylor & Weber

(57) ABSTRACT

A method of producing an antibody fragment for a target antigen includes administering an immunizing mixture containing the target antigen to a cartilaginous fish for at least two times; collecting a blood sample from the cartilaginous fish; extracting RNAs from the blood sample; subjecting said RNAs to reverse transcription to obtain a complementary DNA, and optionally amplifying the cDNA to obtain a mixture of amplified cDNAs followed by purification. Also covered are methods of producing an antibody fragment from a shark; antibody fragments obtained from the method; a kit comprising antibody fragments; and methods of determining the presence and/or amount of a target antigen in a sample.

19 Claims, 13 Drawing Sheets

Specification includes a Sequence Listing.

11,180,544 B2

METHOD OF PRODUCING ANTIBODY FRAGMENT

TECHNICAL FIELD

The present application relates to a method of producing an antibody fragment, in particular but not exclusively, a method of producing an antibody fragment from a heavy chain antibody for a target antigen. The antibody fragment produced may be applied in the biomedical field or drug development.

SEQUENCE LISTING

The Sequence Listing file entitled "sequencelisting" having a size of 9,696 bytes and a creation date of Nov. 7, 2017, that was filed with the patent application is incorporated herein by reference in its entirety.

BACKGROUND OF THE INVENTION

Monoclonal antibodies (mAbs) are widely used for biotechnological and biomedical applications, ranging from affinity purification of target proteins over immunodiagnostics to disease treatments. mAbs have 5 classes of immunoglobulins, 150 kDa in size. Their main structure consists of two identical heavy chains (VH) and two light chains (VL). mAbs are monospecific antibodies that are made by identical immune cells that are all clones of a unique parent cell, in contrast to polyclonal antibodies, which are made from several different immune cells. However, the high cost and low stability of conventional antibodies limit the application of the antibodies in drug discoveries or diagnosis.

In 1993, Hamers-Casterman hit upon the camel derived heavy-chain antibodies (HCAbs) devoid of light chains. In 1995, cartilaginous immunoglobin new antigen receptor also known as IgNAR was found, which is similar to HCAbs in its structure and functions. A heavy-chain antibody consists only of two heavy chains, which can bind antigens despite having only variable heavy-chain domains. Recently, single domain antibodies (sdAbs, also called nanobodies) have been developed. sdAbs is an antibody fragment consisting of a single monomeric variable antibody domain. It is derived from the VHH fragments of camelid HcAbs, and the VNAR fragments of cartilaginous IgNAR.

sdAbs are the smallest antibodies with high stability, specificity, high solubility, and cryptic epitope recognition properties comparing to regular antibodies. They have potential for use in multiple diagnostic and pharmaceutical applications. The fusion of a fluorescent protein to a sdAbs generates a so-called chromobody, which shows increased fluorescence and improved spectral properties. Chromobodies can be used to recognize and trace targets in different compartments of living cells. They can therefore increase the possibilities of live cell microscopy and will enable novel functional studies. In diagnostic biosensor applications, sdAbs may be used prospectively as a tool. Due to their small size, they can be coupled more densely on biosensor surfaces. In addition to their advantage in targeting less accessible epitopes, their conformational stability also leads to higher resistance to surface regeneration conditions. Currently, some sdAbs obtained from camel have entered clinical trials on treating human diseases. However, the costs for camel farming are high which greatly impeded the development of sdAbs.

Antibodies have not yet been successfully produced in simple microbial hosts, because of their large complex structure and the required specific post-translational glycosylation. Hence they have to be produced in mammalian cell lines instead, the cultivation of which is complex and costly (expensive media, long fermentation lead times, scaling issues, use of gases). The resulting antibodies are screened for desired specificities using enzyme-linked immunosorbent assays (ELISAs). However ELISA-based screening is low throughput because only a limited amount (~100 µl) of hybridoma supernatant is available for screening during the initial stages of mAb production and this is typically only sufficient to test each mAb against just one or two antigens. Although nowadays mAbs are well produced and purified under mild conditions, they nonetheless remain sensitive to aggregation, deamination and oxidation.

Size-related limitations of antibodies can be alleviated by using specific parts of antibodies that can be produced in microbial hosts (e.g. Fab regions, variable domains, or sdAbs). A powerful high-throughput technology for evolution-driven engineering is molecular display: the generation of large (poly)peptide libraries and subsequent selection for variants with desired biological and physicochemical properties. The most commonly used display technology is phage display. Due to the sticky nature of filamentous bacteriophages, several extensive washing steps with stringent conditions (e.g., buffers with detergents) are usually required to remove non-specific phages, a laborious process called "biopanning".

Therefore, there remains a strong need for a cost-effective approach to produce sdAb efficiently and provide a diversity for antibody production.

SUMMARY OF THE INVENTION

The present invention provides a cost-effective method for producing high-affinity sdAb. In particular but not exclusively, the method makes use of bacterial production and antibody engineering to produce sdABs. The inventors established a low-cost and highly efficient platform for functional shark-derived sdAbs selection and production to make them attractive in biomedical applications. The platform is based on bacterial display coupled with fluorescence-activated cell sorting (FACS) techniques. This platform can be used to identify target sdAbs with desired properties and can be used to make affinity ligands which are cell-specific.

In a first aspect, the present invention pertains to a method of producing an antibody fragment for a target antigen comprising steps of:
a) administering an immunizing mixture containing the target antigen to a cartilaginous fish for at least two times, preferably at least six times;
b) collecting a blood sample from the cartilaginous fish;
c) extracting RNAs from the blood sample;
d) subjecting said RNAs to reverse transcription to obtain a complementary DNA, and optionally amplifying the cDNA to obtain a mixture of amplified cDNAs followed by purification;
e) inserting the cDNA obtained in step d) into a vector to produce a recombinant plasmid; and introducing the recombinant plasmid into a bacterial cell to form a recombinant cell; and
f) incubating the recombinant cell and extracting the antibody fragment from the incubated recombinant cells.

Preferably, the antibody fragment is a single domain antibody. The cartilaginous fish may be a shark, a ray or preferably a bamboo shark.

In a second aspect, the present invention provides a method of producing an antibody fragment for a target antigen from a shark, comprising steps of:
 a) administering an immunizing mixture containing the target antigen to the shark for at least two times;
 b) collecting a blood sample from the shark; and
 c) extracting RNAs from the blood sample; and
 d) subjecting said RNAs to reverse transcription to obtain a complementary DNA, and optionally amplifying the cDNA to obtain a mixture of amplified cDNAs followed by purification.

Preferably, the method comprises steps of introducing the cDNA to a bacterial surface expression vector. In an embodiment, the cDNA has specific function such as enhancing GFP signal at 488 nm, 421 nm and 525 nm.

In a third aspect, the present invention relates to a DNA encoding for an antibody fragment or an antibody fragment obtained or obtainable from the method. Still further, the present invention relates to a kit comprising the antibody fragment or a DNA sequence encoding for said antibody fragment.

In a further aspect, the present invention pertains to a method of determining the presence and/or amount of a target antigen in a sample, comprising steps of:
 producing an antibody fragment against the target antigen according to the method;
 adding the antibody fragment into the sample, and optionally incubating the mixture for a period of time; and
 performing quantitative or qualitative analysis to determine the presence and/or amount of the target antigen in the mixture.

The antibody fragment in particular single domain antibodies obtained from the method as described herein demonstrates favorable size and cryptic epitope recognition properties, making them attractive in diagnosis and therapy of numerous disease states. Therefore, the present invention provides suitable and effective methods and kit for use in biotechnological and biomedical applications, such as diagnostic kit development and cancer immunotherapies. The antibody fragment of the present invention may be developed as a biosensor.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 4A shows the results obtained in the first shark sample. FIG. 4B shows the results obtained in the second shark sample. FIG. 4C shows the results obtained in the third shark sample.

FIG. 17A shows the positive population on FITC signal, in the first round, of screening by FACS. FIGS. 17B, C, D, E and F come from the same sample used in FIG. 17A and show the result in the third round of screening by FACS. FIG. 17B and FIG. 17C show the positive population on FITC signal. FIG. 17D shows the positive population on APC signal. FIG. 17E shows the positive population on Brilliant Violet 421 signal. FIG. 17F shows the child population of FITC-positive population in FIG. 17C and shows the positive population on both of APC and Brilliant Violet 421 signals.

DETAILED DESCRIPTION OF THE EMBODIMENTS

Figure 1:
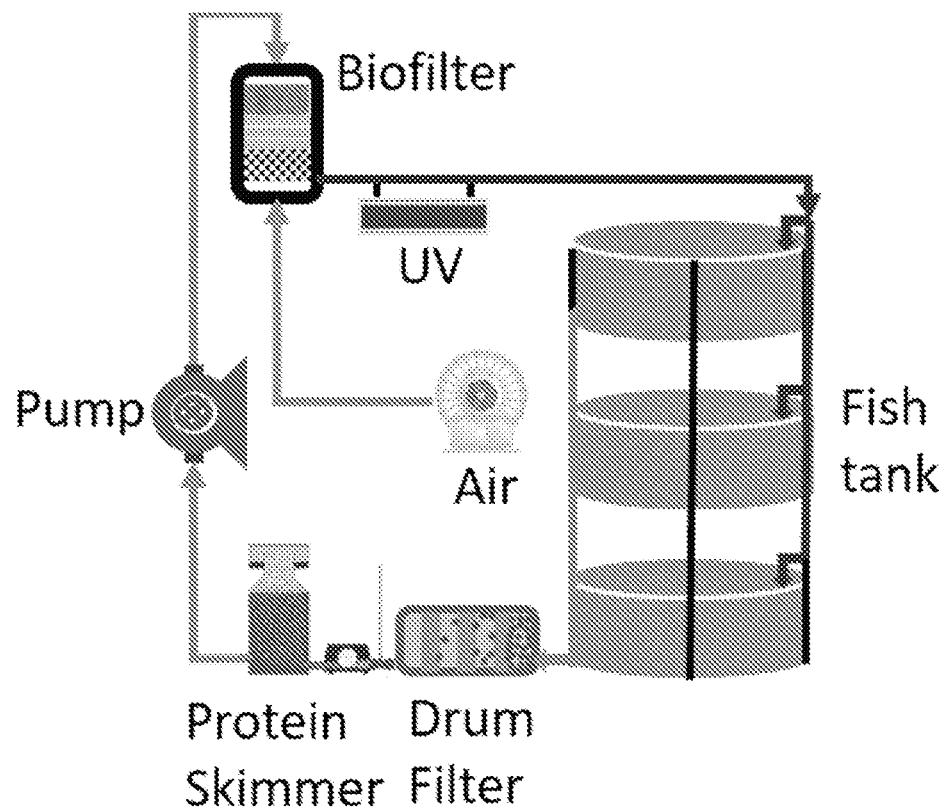
FIG. 1 shows a schematic diagram of a system for shark farming.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in the first aspect provides a method of producing an antibody fragment for a target antigen comprising steps of:
 a) administering an immunizing mixture containing the target antigen to a cartilaginous fish for at least two times;
 b) collecting a blood sample from the cartilaginous fish;
 c) extracting RNAs from the blood sample;
 d) subjecting said RNAs to reverse transcription to obtain a complementary DNA (cDNA), and optionally amplifying the cDNA to obtain a mixture of amplified cDNAs followed by purification;
 e) inserting the cDNA obtained in step d)into a vector to produce a recombinant plasmid; and introducing the recombinant plasmid into a bacterial cell to form a recombinant cell; and
 f) incubating the recombinant cell and extracting the antibody fragment from the incubated recombinant cells.

As used herein, the term "antibody fragment" refers to a portion of an intact antibody molecule (i.e. a portion of a full-length antibody), in particular an active portion of the antibody molecule. The antibody fragment may be expressed by a polynucleotide sequence encoding the antibody fragment sequence. Preferably, the antibody fragment is a single domain antibody (sdAb) which comprises or consists of a single monomeric variable antibody domain. sdAb is also called as nanobody. In general, sdAb has a size of 12 kDa to 15 kDa and has an affinity to bind to a specific antigen. sdAb is sensitive to heat and concentration of urea. The low molecular size and high specificity towards antigens make sdAb an effective tool for diagnosis and therapeutic applications. Compared to regular antibodies, sdAb has higher stability and specificity in particular to bind to hidden antigens which may not be bound by the whole intact antibody.

The term "antigen" refers to a substance that may bind with an antibody or antibody fragment. In general, antigen may be endogenous and generated at normal or abnormal conditions. Abnormal conditions means that the conditions when a subject in particular a mammal or a human is suffering from an illness or a disease such as cancer and inflammatory disease. Antigen may be an artificial substance such as an organic dye or a fluorescent molecule which is capable of binding to the corresponding antibody. In an embodiment, the antigen is metabolic product generated in a subject suffering from a disease. In another embodiment, the antigen is an organic dye or fluorescent molecule such as green fluorescent protein (GFP).

The term "cartilaginous fish" refers to a fish that have a skeleton made of cartilage, rather than bones. In general, the cartilaginous fish may be a species selected from the class of Elasmobranchii or Holocephali. The cartilaginous fish as used herein may be a shark, a skate, or a ray. In an embodiment, the cartilaginous fish is a shark selected from the group consisting of nurse shark, spiny dogfish, and bamboo shark. Preferably, the shark is a bamboo shark from the genus of *Chiloscyllium*. The bamboo shark may be *Chiloscyllium arabicum*, *Chiloscyllium burmensis*, *Chiloscyllium griseum*, *Chiloscyllium hasselti*, *Chiloscyllium indicum*, *Chiloscyllium plagiosum*, or *Chiloscyllium punctatum*. In an embodiment, the bamboo shark is *Chiloscylium punctatum*. The size of a bamboo shark is relatively small compared to other species of shark and therefore the operator can easily breed the bamboo shark. Also thanks to the small size of the bamboo shark, it saves efforts to administer the immunizing mixture to the bamboo sharks and collect the blood sample from them compared to camel. Accordingly, the use of cartilaginous fish in particular bamboo shark saves costs in production of antibody fragment. Also, it may be a faster approach to derive sdAb from an animal model.

The phrase "immunizing mixture" refers to a mixture containing the target antigen for triggering an immune response in the cartilaginous fish in particular a shark. The immunizing mixture preferably comprises the target antigen as described above and optionally a Freund's Adjuvant (FA). The Freund's Adjuvant may be Complete or Incomplete Freund's Adjuvant. Complete Freund's Adjuvant (CFA) comprises inactivated and dried mycobacteria in mineral oil while the Incomplete Freund's Adjuvant (ICFA) does not contain the mycobacterial components but only comprise water in mineral oil. FA is used as a simulator to induce activation or increase the activity of an immune response.

The step a) where the immunizing mixture is administered to the cartilaginous fish may be called as an immunization. In an embodiment, the cartilaginous fish in particular a shark is administered with the immunizing mixture once per month for at least 2 or at least 3 months. In the first immunization, the immunizing mixture may be a mixture comprising or consisting of the target antigen and the CFA. For the subsequent immunization, i.e. the second and third immunization, the immunizing mixture may be a mixture comprising or consisting of the target antigen and the ICFA. In another embodiment, the cartilaginous fish in particular a shark is administered with the immunizing mixture per month for at least 4 times, at least 5 times, or at least 6 times. The immunizing mixture for the first immunization preferably comprises or consists of the target antigen and the CFA. For the rest of the immunizations, the immunizing mixture may comprise or consist of the target antigen and the ICFA.

After immunization, a blood sample is collected from the cartilaginous fish. Preferably, the cartilaginous fish is anesthetized for immunization and blood collection. In the step b), a blood sample of about 1 to about 5 ml, about 2 to about 4 ml, or about 2 to about 3 ml is collected preferably using a syringe containing or being rinsed with an anti-coagulating agent such as sodium citrate.

Next, the blood sample is subject to separation for separating blood cells and plasma. The blood sample may be centrifuged to obtain two separate layers. In an embodiment, the blood sample is centrifuged at the highest speed for at least 1 minute to obtain two separate layers. The upper layer, i.e. the plasma layer, preferably contains immunoglobulin new antigen receptors (IgNARs) released from the blood cells in particular from white blood cells, and the lower layer contains the separated blood cells. In an embodiment, a Western blot analysis may be performed to determine if cartilaginous fish produces the desired antibody.

In order to extract the RNAs which preferably comprise sequences encoding the antibody fragment from the collected blood sample, the step c) comprises a step of lysing the separated blood cells to release the RNAs. Optionally, immunoglobulin new antigen receptors (IgNARs) present in the plasma layer are separately isolated for protein analysis such as Western blot analysis in particular to confirm if the cartilaginous fish successfully generated the desired antibody.

The method of the present invention may involve a one-step amplification or two-step amplification of the antibody fragment. For the one-step amplification, after the extraction of the RNAs from the blood sample, the extracted RNAs may subject to reverse transcription to construct complementary DNAs (cDNA) and cDNAs will then proceeded with amplification using primers, and the amplified DNA products are further purified. The produced cDNA is preferably the DNA sequence encoding the desired antibody. In particular, a polymerase chain reaction (PCR) may be performed to amplify the antibody fragments. In an embodiment, the primer for antibody fragment amplification comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and a combination thereof, as shown below. Preferably, more than one primer is used.

```
F1R1:
                                          (SEQ ID NO: 1)
F1 GGG TAG ACC AAA CAC CAA GAA C (SEQ ID NO: 2)
R1 GAG GAG ACT GAC TAT TGG TGG AG

F2R2:
                                          (SEQ ID NO: 3)
F2 AAAAGAGACGGACGAATCACTGACC (SEQ ID NO: 4)
R2 CGGTCAGTCCGGTGCC

F3R3:
                                          (SEQ ID NO: 5)
F3 WTTCACAGTCASARKGGTSCC (SEQ ID NO: 6)
R3 ATGGCCSMACGGSTTGAACAAACAC

F4R4:
                                          (SEQ ID NO: 7)
F4 GGG AAGCTT GCC GCA CGG GTT GAA CAA ACA CCG (SEQ ID NO: 8)
R4 GGC GAATTC CAC AGT CAG AGG GGT GCC GCC TCC
```

The purification may be conducted by using a buffer solution and centrifugation to remove the undesirable impurities such as unreacted primers, dNTPs, enzymes and other impurities. The person skilled in the art is aware of possible and commercially available methods for purifying the amplified DNA product, such as PCR Clean-up kit and Gel Clean-up kit.

For the preferred two-step amplification, it further includes the step e) and f) by making use of the recombinant DNA technology to enlarge the scale of production and screen the desired antibody fragment.

Preferably, the step e) comprises steps of:
  inserting the cDNA obtained in step d) into a vector to produce a recombinant plasmid;
  optionally purifying the recombinant plasmid by precipitation using an alcohol; and
  introducing the recombinant plasmid or the purified recombinant plasmid into a bacterial cell to form a recombinant cell.

The term "vector" refers to a replicon in which another polynucleotide segment is inserted therein to bring about the replication and/or expression of the attached polynucleotide segment. In the present invention, the vector comprises an intimin domain which encodes intimin for protein expression on the outer membrane of a bacterial cell, in particular on the outer membrane of E. Coli cell. Preferably, the vector comprises a sequence as shown in SEQ ID NO: 9 which corresponds to a truncated intimin gene. In an embodiment, the vector is a pET32(a+) expression vector derived from E. Coli and is modified to comprise the SEQ ID NO: 9. The modification may be made by using digestive enzymes such as EcoRI and HindIII at the respective sites.

The cDNA obtained in step d), in particular a DNA sequence encoding the antibody fragment, is then inserted to the vector via ligation to produce a recombinant plasmid. Preferably, the cDNA is digested by enzymes such as EcoRI and HindIII to create cleavage sites for ligation with the vector. After the insertion, the cDNA is preferably infused with the intimin domain as such the sdAb, after transformation, can be expressed on the outer cell membrane on the transformed bacterial cell and thus be recognized by the target antigen.

In an embodiment, the molar ratio of the vector to the cDNA is in a range of about 5:1 to about 9:1. In particular, the molar ratio of the vector to the cDNA is about 9:1. The higher the amount of the vector used, the higher the transformation efficiency obtained.

After the ligation, the recombinant plasmid may be purified by precipitation before introduction into the bacterial cell. In particular, the precipitation is performed by mixing the recombinant plasmid product with an alcohol and a salt. The salt may be sodium acetate or the like. The mixture is then subject to centrifugation and the supernatant containing soluble impurities is discarded. This step may be repeated to obtain the recombinant plasmid at a higher purity. The person having the ordinary skills in the art is aware of suitable methods for purifying DNA sequences, for instance commercial kits may be applied.

Subsequently, the purified recombinant plasmid is introduced to the bacterial cell preferably an E. Coli cell to form the recombinant cell for replication. Such an introduction may also be called as transformation. In a particular embodiment, the E. Coli cell is a strain which is capable of expressing Shuffle T7 protein. A person having ordinary skills in the art is aware of suitable methods of transformation. For instance, the transformation may be carried out by conducting electrophoresis, heat shock, or physical injection. Physical injection of the purified recombinant plasmid may be performed by using nanoneedles.

After transformation, the recombinant cell is incubated for a period of time to allow sufficient replication of the cDNA strand in the bacterial cell. The length of the incubation depends on the growth rate of the bacteria, the incubation conditions and the desired amount of antibody fragments to be produced. The person having the skills in the art is capable of adjusting the parameters for incubating the recombinant cells. Lastly, the bacterial cells are collected and lysed for extraction of the antibody fragment.

The present invention provides a method of producing antibody fragment in particular a single domain antibody from a shark in particular a bamboo shark. The method enables mass production of the shark-derived sdAbs at a reduced cost compared to that of camel-derived sdAbs. The combination of fish farming, recombinant DNA technology and bacterial display allows the method to produce sdAb in an effective manner. The sdAb obtainable or obtained from the method may be applied in various applications.

In a second aspect, the present invention pertains to a method of producing an antibody fragment for a target antigen from a shark, comprising steps of:
  a) administering an immunizing mixture containing the target antigen to the shark for at least two times;
  b) collecting a blood sample from the shark; and
  c) extracting RNAs from the blood sample; and
  d) subjecting said RNAs to reverse transcription to obtain a cDNA, and optionally amplifying the cDNA to obtain a mixture of amplified cDNAs followed by purification.

The antibody fragment and the target antigen are as described above. In particular, the antibody fragment may be a single domain antibody (sdAb). Preferably, the shark is a bamboo shark from the genus of *Chiloscyllium*. The bamboo shark may be *Chiloscyllium arabicum, Chiloscyllium burmensis, Chiloscyllium griseum, Chiloscyllium hasselti, Chiloscyllium indicum, Chiloscyllium plagiosum*, or *Chiloscyllium punctatum*. In an embodiment, the bamboo shark is *Chiloscylium punctatum*.

In an embodiment, the immunizing mixture, as described above, comprises the target antigen and a Freund's Adjuvant and is administered to the shark once per month for at least 3 times, at least 4 times, at least 5 times or at least 6 times. Preferably, the shark is administered with the immunizing mixture once per month for 6 times for immunization of a particular target antigen. In a particular embodiment, the target antigen is a fluorescent molecule or an organic dye.

After immunization, the blood sample is collected from the shark for extraction of the RNAs. As mentioned earlier, the extracted RNAs may be subject to reverse transcription and amplification to produce cDNA using primers as described above.

The method further comprises a step of inserting the cDNA which encodes the desired antibody fragment into a vector to form a recombinant plasmid, wherein the vector comprises an intimin domain; and introducing the recombinant plasmid to a *E. Coli* cell to form a recombinant cell. The recombinant cell may be subsequently incubated. Lastly, the antibody fragment is extracted from the incubated recombinant cells.

In a third aspect, the present invention provides an antibody fragment obtained or obtainable from the method as described herein. Preferably, the antibody fragment is a single domain antibody derived from a shark in particular a bamboo shark. The current commercially available sdAbs are produced from camelids such as camel and llama. However, the cost of camelid farming of exceptionally high and thus impedes the development of sdAbs. For the present invention, the application of bamboo shark, i.e. a small-size shark, is a possible animal model for the production of sdAbs. The bamboo shark can be bred artificially and the farming cost is relatively low. Further, IgNARs obtained from sharks and according to the present invention have high stability and may trigger a stronger immune response. The strong immune response may be due to high concentration of urea in the blood and low homology between bamboo shark and human. Accordingly, the cartilaginous fish-derived sdAbs in particular shark-derived sdAbs possess are different from those obtained from camel and possess obvious advantages on triggering immune response and possess high specificity towards antigens.

In particular, the single variable new antigen receptor domain antibody fragments (VNARs) derived from shark IgNARs represent the smallest known immunoglobulin-based protein scaffolds. As single domains, they demonstrate favorable size and cryptic epitope recognition properties, making them attractive in diagnosis and therapy of numerous disease states. Therefore, the antibody fragment as produced according to the method is suitable for use in biotechnological and biomedical applications, such as diagnostic kit development and cancer immunotherapies.

In a fourth aspect, there is also provided a kit comprising the antibody fragment. Optionally, the kit further comprises an instruction manual describing how to apply the antibody fragment and/or the original of the antibody fragment. The kit may further comprise another antibody as a secondary antibody for research or diagnostic purpose.

Also, it would be appreciated that the antibody fragment may be provided by way of a recombinant vector or recombinant cell. For instance, there are provided a recombinant vector comprising an intimin domain and an antibody fragment, and a recombinant cell comprising the recombinant vector.

In a further aspect, there is provided a method of determining the presence and/or amount of a target antigen in a sample, comprising steps of:
  producing an antibody fragment against the target antigen according to the method as described above;
  adding the antibody fragment into the sample, and optionally incubating the mixture for a period of time; and
  performing quantitative or qualitative analysis to determine the presence and/or amount of the antibody fragment in the mixture.

Preferably, the sample is a biological sample obtained from a subject which may be a mammal or human. In an embodiment, the subject is a patient suffering from a disease such as inflammatory disease, neuro-immune disease, gastrointestinal disease, cardiovascular disease, immune disease, injury, bacterial infection, cancer or the like. The biological sample may be blood, plasma, serum, saliva, urine, feces or the like obtained from the subject.

Preferably, the sample is a blood sample, plasma sample, serum sample or saliva sample. The sample may be optionally treated to break down the cells to release antigens from the cells. The addition of the antibody fragment allows the antibody fragment to bind to the antigens present in the samples. The conditions of incubation, optional washing or rinsing, are adjustable and would be appreciated by the person having the ordinary skills in the art. Lastly, a quantitative or qualitative analysis is performed to determine the presence and/or the amount of the target antigen in the mixture.

In an embodiment, the quantitative or qualitative analysis may be selected from gel electrophoresis, Western blot analysis, flow cytometry analysis, enzyme-linked immunosorbent assay (ELISA), fluorescence-activated cell sorting (FACS), or other suitable analysis known in the field. Accordingly, the present invention provides an effective quantitative or qualitative method for diagnostic purpose or research application. In particular, it is useful for determining whether a subject is carrying the target antigen, and for determine the health condition of a subject.

Still further, there is provided a method of diagnosis by using the sdAb produced according to the present invention. The obtained sdAb may be used to detect the presence of an antigen in a sample, wherein the sample may be a biological sample obtained from a human or a patient suffering from a particular disease. In an embodiment, the obtained sdAb is fused or conjugated with a fluorescent protein or dye to form a complex. When the complex binds on the antigen in the sample, an operator can measure the level of fluorescence or light absorbance to determine the presence/absence and/or amount of the target antigen in the sample. Accordingly, the sdAb produced according to the method as disclosed herein can be used as a biosensor. I.e. it directs to use of the antibody fragment in the manufacture of a medicament for diagnosis or in the manufacture of a biosensor. This is advantageous in that the method provides sdAb for clinical use and scientific research.

Furthermore, the sdAb produced may be used in treatment for binding to a target antigen or target cells in a subject. For instance, it may be developed to inhibit the overly expressed cancer cells, or bind to a target antigen thereby triggering an immune response to fight against the target antigen. Given the small molecular size (high permeability to pass through the blood-brain-barrier), high specificity to target antigen and low cytotoxicity, it may be used in a therapy for treating neuro-immune disease. It may be applied in photothermal therapy or chemotherapy. I.e. it directs to use of the antibody fragment in the manufacture of a medicament.

EXAMPLES

Example 1

Preparation of sdAb from Bamboo Sharks

Shark Farming

Bamboo sharks are held in large, indoor tanks (250 L) supplied by flow-through seawater at about 21° C. Bamboo sharks are fed with frozen shrimp meat and eel powder once per day. FIG. 1 shows the system for shark farming. Particularly, the fish tanks are connected to a filtering system. The filtering system has a pump, a drum filter connected to a protein skimmer, and a biofilter for filtering organic waste from the water flow. A UV sterilizer may be provided to prevent fish diseases and control algae growth in the fish tanks.

In an example, before immunization and blood collection, the bamboo sharks are anesthetized with tricaine methanesulfonate (MS-222). Particularly, 5 g of MS-222 are added in 50 L seawater, i.e. about 0.1 g/L MS-222, and the seawater are provided in a continuous air and water flow to the bamboo sharks. The conditions of the anesthetized bamboo sharks are continuously monitored after anesthetization. After 3 minutes, the bamboo sharks are either administered with an immunizing mixture or subject to blood collection. After immunization or blood collection, the bamboo sharks are transferred to another fish tank for recovery. The operation time for the immunization and blood collection is preferably controlled within 10 minutes after anesthetization.

Immunization

The bamboo sharks are subject to immunization monthly with an immunizing mixture comprising an antigen and Complete or Incomplete Freund's Adjuvant (CFA or ICFA). The immunizing mixture is administered subcutaneously to the bamboo sharks via lateral fins. The bamboo sharks are immunized for at least 6 times for one kind of antigen.

In this example, whole cell proteins of fetal mouse liver cells, green fluorescent protein (GFP) and whole cell membrane proteins of mouse red blood cells are used as antigens. The immunizing mixture containing whole cell proteins of fetal mouse liver cells is prepared by:

adding 20 μl RIPA buffer solution per 1 million cells to $3.0 \times 10^7$ fetal mouse liver cells for cell lysis and protein extraction, and placing the mixture on ice for 30 min; and separating the whole cell proteins from the lysed cells via centrifugation; and mixing 600 μl of separated whole cell proteins and 600 μl of a Freund's Adjuvant (at a volume ratio of 1:1) for 1 h using a 2.5 ml syringe and its connector until a white emulsion is formed, in which the white emulsion is the immunizing mixture for injection.

The Freund's Adjuvant may be CFA or ICFA. In particular, CFA is applied for preparing an immunizing mixture for the first immunization and ICFA is applied for preparing an immunizing mixture for subsequent immunization. When mixing the separated whole cell proteins and the Freund's Adjuvant, it is important to not introduce bubbles in the mixture. After mixing, about 1000 μl remain. Each shark is injected with 500 μl of the immunizing mixture.

An immunizing mixture containing green fluorescent protein (GFP) is prepared by mixing green fluorescent protein with the Freund's Adjuvant. In particular, 400 μg of GFP is dissolved in 600 μl PBS. The GFP solution is then mixed with 600 μl of the Freund's Adjuvant. An immunizing mixture containing whole cell membrane proteins of mouse red blood cells (RBC) is prepared in a similar way as that containing whole cell proteins of fetal mouse liver cells described above.

4 sharks are divided into 2 groups, and the bamboo sharks of each group are administered with GFP-containing immunizing mixture or RBC protein-containing immunizing mixture. An additional group containing 2 sharks is administered with the RBC-protein containing immunizing mixture for 6 times followed by administration of the immunizing mixture containing whole cell proteins of fetal mouse liver cells.

Figure 2A:
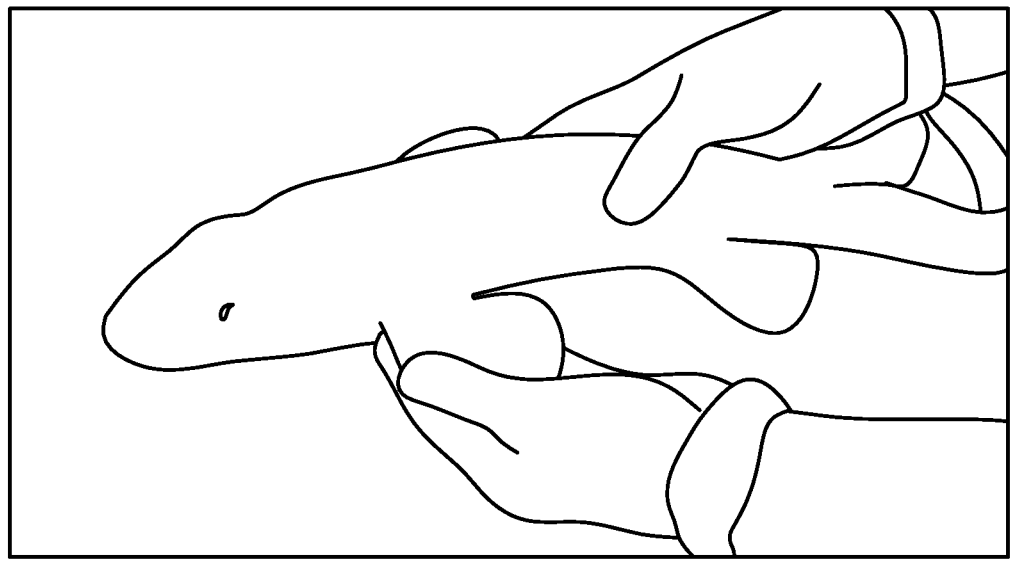
FIG. 2A is a photo of a bamboo shark used in an embodiment of the present invention.
Figure 2B:
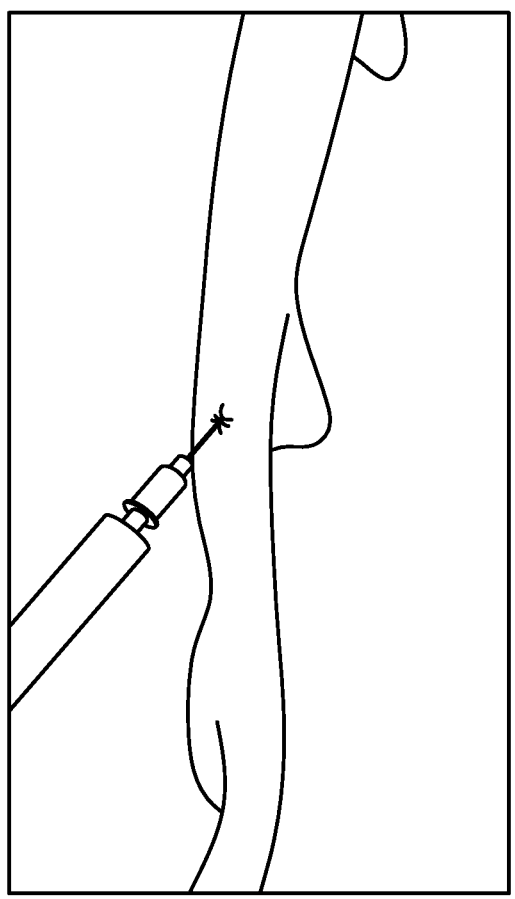
FIG. 2B shows how the blood is collected from the bamboo shark.

With reference to FIGS. 2A and 2B, the prepared immunizing mixture is administered to each of bamboo shark via hypodermic injection at the position between pectoral and pectoral fins, from the dorsal side.

Blood Collection 2 weeks after the final administration of the immunizing mixtures, blood samples are collected from the caudal vein of immunized bamboo sharks. The caudal vein in bamboo sharks can be found by palpating the sharks and then placing the needle in front of the cartilage, advancing the needle slowly with slight negative pressure in syringe until a flash in obtained. Particularly, the needle is directed anteriorly at an angle of 30 to 90°, relative to the body of the bamboo shark, and inserted until the needle tip meets cartilage (approximately 4 cm for a 10 kg shark) to penetrate the vessel.

2 to 3 ml of blood are obtained from each of the bamboo shark. For 1 kg bamboo shark, it contains about 20-30 ml of blood, i.e. about 2-3% of the weight refers to the total weight of the blood. The blood is collected with approximately 200 μl sodium citrate in the syringe barrel to inhibit coagulation. The blood is then immediately transferred into blood-collecting tube. Generally, 1 to 1.5 ml of blood per shark is used for RT-PCR and cDNA amplification. About 75% of the blood obtained from bamboo shark is plasma. At least $2 \times 10^5$ white blood cells in about 80 μl whole blood (55% plasma and 45% formed elements for human blood) are needed for one sample.

Centrifugation is performed to separate blood cells and plasma in the blood samples under the conditions of 1,000 g for 5 min. The separated plasma and anti-coagulated whole blood cells are stored at −80° C. until use. 100 μl of anti-coagulated whole blood cells are mixed with 750 μl of Trizol, and the mixture are homogenized by pipetting up and down for several times.

Figure 3:
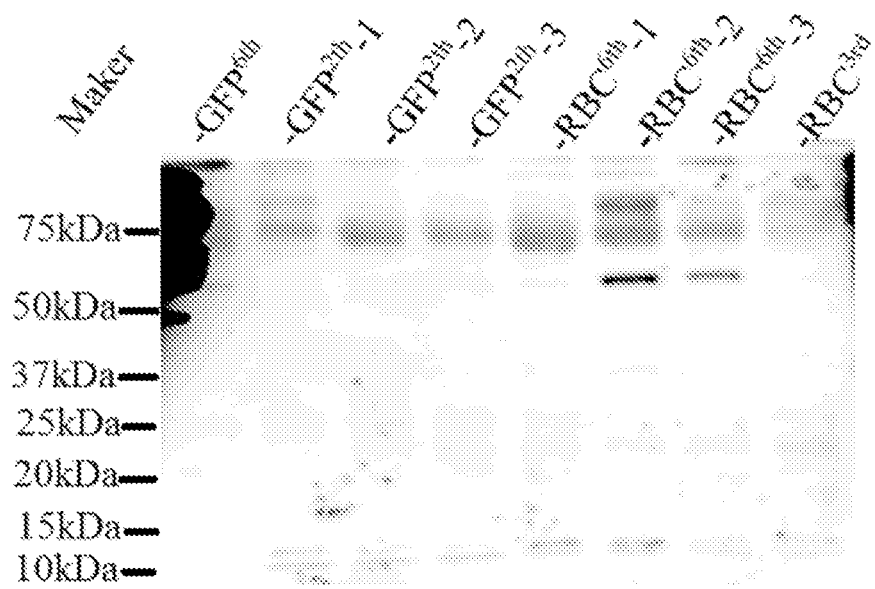
FIG. 3 shows the protein expression of IgNARs (~60 kDa) in the plasma of the sharks after being immunized for 6 times.
Figures 4A, 4B, 4C:
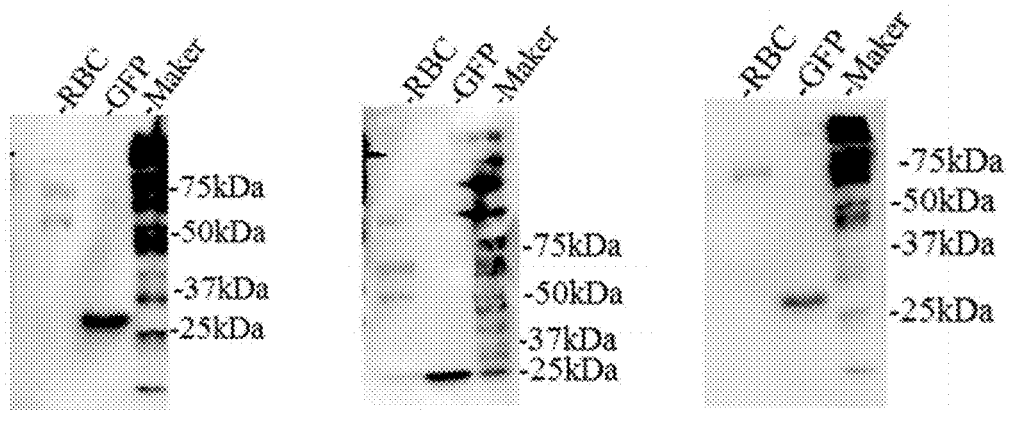
FIGS. 4A, 4B, and 4C show the protein expression of the target IgNARs in the plasma of all sharks which immunized by using RBC-containing immunizing mixture. The target IgNARs are specific to GFP and mouse RBC membrane proteins. All plasma were treated with anti-horn shark IgNAR antibody (1:3000) as a primary antibody and anti-rabbit IgG-HRP conjugate antibody (1:2000) as a secondary antibody.
Figure 5:
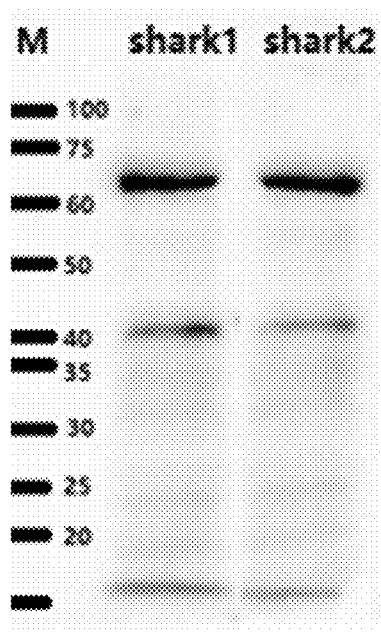
FIG. 5 shows the protein expression of IgNARs in the plasma of sharks which immunized with an immunizing mixture containing the fetal mouse liver cells. The IgNARs specifically bind ~40 kDa and ~65 kDa proteins from metal mouse liver cells. The plasma was incubated with immunized shark plasma (1:100); anti-horn shark IgNar antibody (1:3000); and subsequently anti-rabbit IgG-HRP conjugate antibody (1:3000).

Since IgNAR antibodies have been produced and released by lymphocytes into the plasma, the separated plasma can be used to detect if target-specific IgNARs have been produced. FIG. 3 shows the protein expression of the IgNARs in the plasma of the sharks after 6-time immunization. The plasma samples were incubated with 1:1000 anti-horn shark IgNAR antibody and 1:2000 anti-rabbit IgG-HRP conjugate antibody. FIGS. 4A to 4C show the protein expression of the target IgNARs in the plasma of all sharks which immunized by using RBC-containing immunizing mixture. The target IgNARs are specific to GFP and mouse RBC membrane proteins. Similarly, FIG. 5 shows the protein expression of IgNARs in the plasma of sharks which immunized with an immunizing mixture containing the fetal mouse liver cells.

Example 2

Preparation of Single-Domain Antibody Fragments

All available sequences for IgNAR are collected and extracted. Based on the identified sequences, four sets of primers are prepared for amplification, as shown below:

```
F1R1:
                                                (SEQ ID NO: 1)
F1 GGG TAG ACC AAA CAC CAA GAA C (SEQ ID NO: 2)
R1 GAG GAG ACT GAC TAT TGG TGG AG

F2R2:
                                                (SEQ ID NO: 3)
F2 AAAAGAGACGGACGAATCACTGACC (SEQ ID NO: 4)
R2 CGGTCAGTCCGGTGCC

F3R3:
                                                (SEQ ID NO: 5)
F3 WTTCACAGTCASARKGGTSCC (SEQ ID NO: 6)
R3 ATGGCCSMACGGSTTGAACAAACAC

F4R4:
                                                (SEQ ID NO: 7)
F4 GGG AAGCTT GCC GCA CGG GTT GAA CAA ACA CCG (SEQ ID NO: 8)
R4 GGC GAATTC CAC AGT CAG AGG GGT GCC GCC TCC
```

F1R1 and F2R2 are specifically designed based on the sequence alignment. F3R3 is derived from Zielonk et al., J Biotechno 2014. F4R4 is designed based on the other three primers with the additions of HindIII and EcoRI.

A reverse transcription PCR (RT-PCR) is conducted to obtain complementary DNA (cDNA) products. Table 1 and Table 2 outline the parameters of the RT-PCR.

TABLE 1

Parameters of the PCR system

| | Volume/per reaction (μl) | |
|---|---|---|
| 10x DreamTaq Buffer | 5 | 40 |
| dNTP Mix, 2.5 mM each | 4 | 32 |
| Forward primer, 10 μM | 5 | 40 |
| Reverse primer, 10 μM | 5 | 40 |
| Template DNA | 5 | 40 |

TABLE 1-continued

Parameters of the PCR system

| | Volume/per reaction (μl) | |
|---|---|---|
| DreamTaq DNA polymerase, 5 U/μl | 0.25 | 2 |
| Rnase-free water | 25.75 | 206 |
| Total volume | 50 | 400 |

TABLE 2

Conditions for Thermal Cycling

| Step | Temperature °C. | Time | Number of cycles |
|---|---|---|---|
| Initial denaturation | 94 | 2 min | 1 |
| Denaturation | 94 | 30 s | 40 |
| Annealing | 69 | 30 s | |
| Extension | 72 | 40 s | |
| Final Extension | 72 | 7 min | 1 |
| | 4 | hold | |

Figure 6:
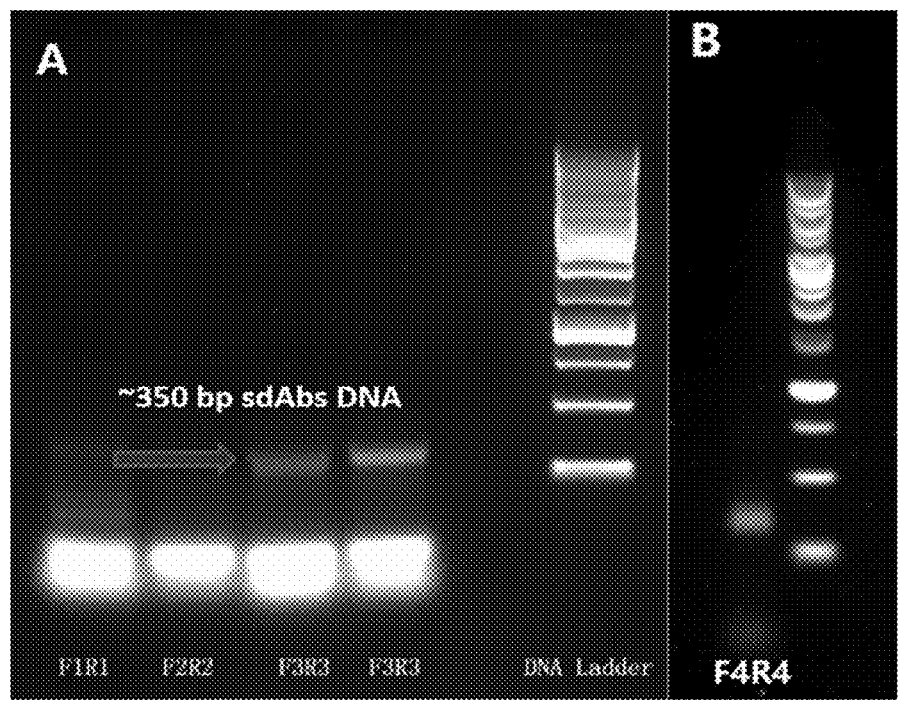
FIG. 6 shows the expressions of cDNA products prepared from four designed primers.

After amplification, the products are subject to agarose gel electrophoresis to determine cDNA products. The expressions of the cDNA products prepared from the four primers are as shown in FIG. 6.

Figure 7:
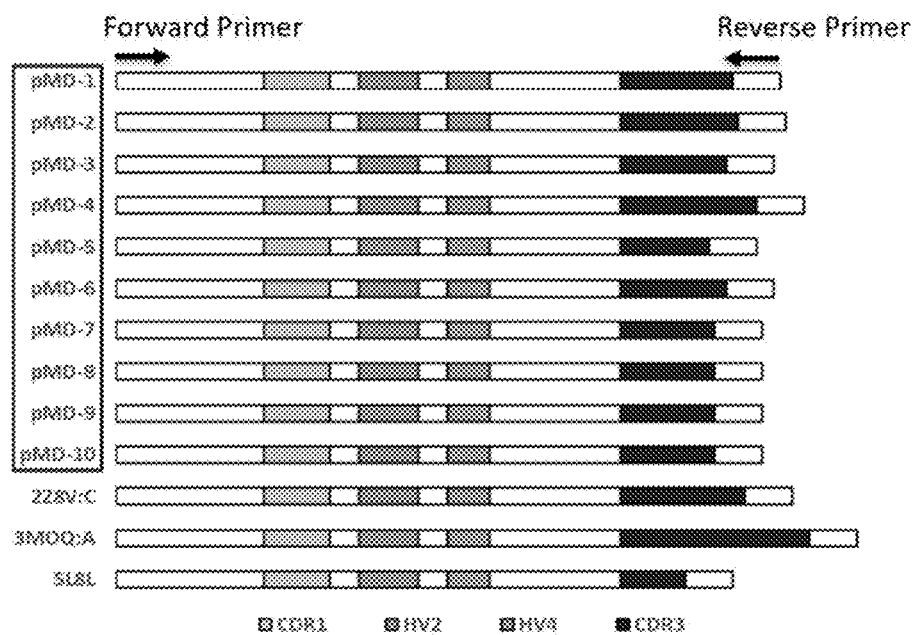
FIG. 7 shows the protein sequence alignment of 10 cloned inserts (pMD-1 to pMD-10) with 3 shark sdAbs from RCSB PDB (2Z8V:C, 3MOQ:A, and 5L8L).

The sdAb cDNA products are then purified using a Clean-up kit to remove unreacted primers and dNTPs, enzymes and other impurities. Preferably a PCR Clean-up kit is applied. And then the purified cDNA are ligated into pMD20-T vector using TakaRa Mighty TA-Cloning Kit. The ligation reaction is transformed into DH5a competent cell as the protocol of TakaRa Mighty TA-Cloning Kit described. The blue white screening was used to screen the transformed DH5a. 10 white colonies were picked up and sent to sequencing. The 10 cloned inserts with lengths between 334~348 bp were made alignment with 34 shark sdAbs as known and were then confirmed as sdAbs. FIG. 7 shows the sequence alignment of the 10 cloned inserts in 3 shark sdAbs derived from RCSB PDB (2Z8V:C, 3MOQ:A, and 5L8L). Complementarity determining regions (CDR) and hypervariable loops (HV) are shown in their relative positions. The identical or conservative residues are shown in empty box. The conserved termini dictated by the oligonucleotide primer sequences are used in library construction.

Next, the purified sdAb DNA was digested by using enzymes EcoRI and HindIII using the following protocol. The same protocol is applied to digest a vector for subsequent ligation.

TABLE 3

Protocol for double digestions of sdAb

| Component | 50 μl Reaction mixture |
|---|---|
| DNA | 1 μg |
| 10X CutSmart Buffer | 5 μl |
| HindIII-HF | 1 μl (or 20 units) |
| EcoRI-HF | 1 μl (or 20 units) |
| Nuclease-free water | Fill the reaction mixture to 50 μl |

The digested products are subsequently purified by use of another Clean-up kit. The Clean-up kit in this step is preferably Gel Clean-up kit which achieves a high degree of purification. The resultant sdAb DNAs are linear sdAb fragments.

Example 3

Preparation of a Plasmid Containing sdAb DNA

Preparation of Vector pET32(a+) vector is used for ligation with the sdAb obtained in Example 2. In particular, a pET32(a+)-Int comprising a truncated intimin gene is synthesized and cloned by Guangzhou IGE Biotechnology Ltd.

Figure 8:
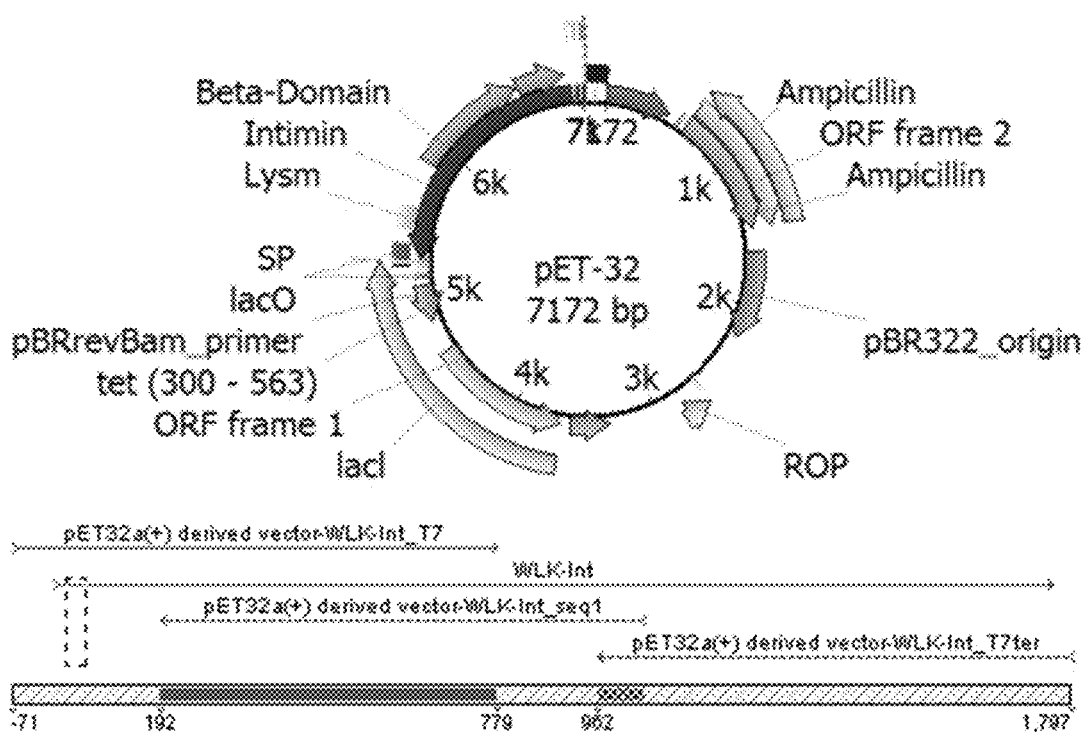
FIG. 8 illustrates the sequence arrangement of a vector used in an embodiment of the present invention.

The sequence of truncated intimin gene is shown as SEQ ID NO: 9. The sequence has 1-559 residues and a length of 1677 bp. FIG. 8 illustrates the sequence arrangement of the vector.

Figure 9:
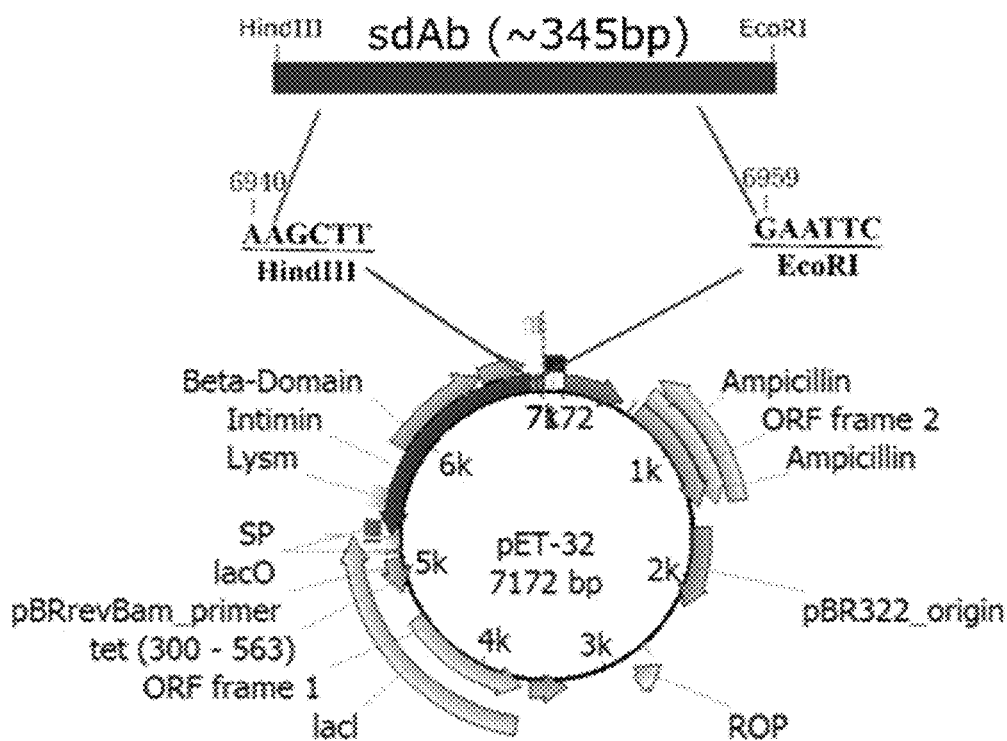
FIG. 9 is a diagram illustrating the incorporation of sdAb into the vector of FIG. 4 after ligation.
Figure 10A:
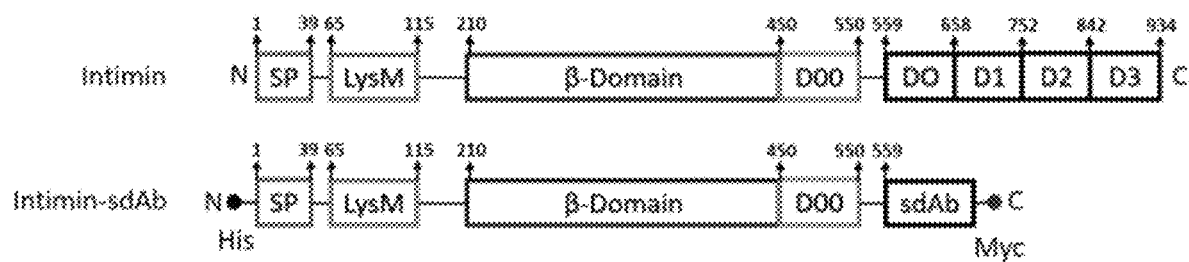
FIG. 10a is a schematic diagram showing the fusion of intimin and sdAb DNA.
Figure 10B:
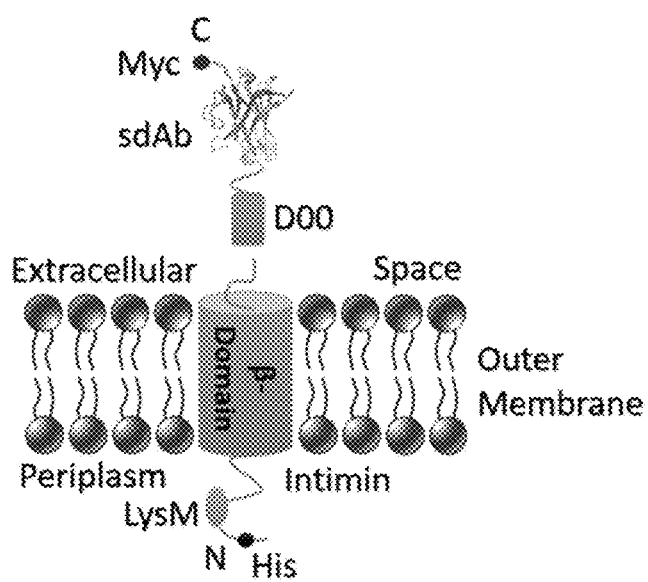
FIG. 10b shows a proposed model of intimin-sdAb fusion in the outer membrane, with N-terminal LysM domain in the periplasm, barrel with linker in the OM, while C-terminal D00 and sdAb domains exposed to the extracellular milieu.

The vector is digested by enzymes EcoRI and HindIII at the respective sites for ligation with the sdAb obtained in Example 2. FIG. 9 illustrates the incorporation of sdAb after ligation, i.e. the sdAb DNA is ligated into the same sites cleaved by the enzymes. FIG. 10a is a schematic diagram showing the fusion of intimin and sdAb DNA. In particular, the intimin-sdAb fusion includes N-terminal signal peptide (SP), LysM and β-domains, and secreted D00-D3 Ig-like, lectin-like domains, and sdAb domain, in which the sdAb domain replaces D0-D3 originally placed in the truncated intimin gene. FIG. 10b shows a proposed model of intimin-sdAb fusion in the outer membrane, with N-terminal LysM domain in the periplasm, barrel with linker in the OM, while C-terminal D00 and sdAb domains exposed to the extracellular millieu. The His-tag and myc-tag epitopes flanking the intimin and the sdAb domain are indicated.

Ligation of sdAb DNA and Vector

The ligation is carried out according to the following steps:
- optionally thawing and re-suspending T4 DNA ligase buffer at room temperature;
- adding 2 µl 10×T4 DNA ligase buffer, 100 ng of the digested vector (having a length of about 7149 bp), 42.8 ng of the sdAb obtained in Example 2 (having a length of about 345 bp), 1 µl of T4 DNA ligase and nuclease-free water which tops up the reaction volume to 20 µl in a micro-centrifuge tube on ice;
- gently mixing the mixture by pipetting up and down, and optionally microfuge briefly; and
- optionally incubating the mixture at 16° C. overnight if there are cohesive ends, or at room temperature for 1 h and then 16° C. for 3 h.

The molar ratio of sdAb (insert) to vector is 9:1. This molar ratio achieves the best ligation efficiency based on the following electroporation results.

Figure 11:
FIG. 11 shows the results obtained from the electrophoresis.

An agarose gel electrophoresis is performed to determine whether the sdAb is inserted into the vector. FIG. 11 shows the results obtained from the electrophoresis. The plasmids in the ligation mixture are transformed into T7 cells and the cells are allowed to grow on LB/Amp plate to form visible colonies. Then a colony is randomly picked and subject to 5 ml of LB culture for carrying out plasmid Miniprep. The plasmid obtained is proceeded with double-digestion using EcoRI and HindIII. Lastly, the digestion mixtures are processed with agarose gel electrophoresis (1% gel, run 50 mins at 100V).

DNA Precipitation

Before electroporation, DNA precipitation is performed on the ligated products to increase the ligation efficiency, remove undesirable salts, and increase the DNA concentration. The following steps are taken
- preparing a reaction mixture for each ligated sample by mixing 50 µl of a ligated DNA sample, 100 µl of 1.5M sodium acetate solution (pH 5.2) and 350 µl of 100% ethanol;
- keeping the mixture at −20° C. for 2 h, and then at room temperature for 15 min;
- performing centrifugation at a maximum speed for 20 min, discarding the supernatant, adding 500 µl of 70% ethanol to the residue to remove impurities, and keeping it at room temperature for 15 min, in which this step is carried out for at least two times;
- performing centrifugation again at a maximum speed for 20 min, and discarding the supernatant; and
- drying the residue at room temperature or via a drying machine.

A library of $10^6$ is used for screening GFP positive sdAb. This library is from the immune library of sdAbs against GFP. The amplified sdAb gene segments were cloned into the EcoRI and HindIII sites of pET32(a+) vectors, generating an E. coli display immune library of ~1×10$^6$ clones.

After DNA precipitation, purified recombinant DNA plasmids containing the sdAb gene sequence are obtained.

Example 5

Introduction of the Recombinant Plasmids to Cells

Preparation of Electrocompetent Cells

Shuffle T7 competent E. Coli cells are grown at 30° C. with vigorous shaking at 250 rpm in 500 ml LB medium in

TABLE 4

The electroporation results obtained after directly adding the ligation products to electrocompetent cells.

| # | Strain | Cuvette (cm) | Model | Bacterial vol. (µl) | DNA conc. (pg/µl) | DNA quantity used (pg) | Dilution folds before plating (100 µl for plating) | Colonies in one plate (only one plate per group) | Transformation efficiency (cfu/µg DNA) |
|---|--------|--------------|-------|---------------------|-------------------|------------------------|----------------------------------------------------|---------------------------------------------------|----------------------------------------|
| 1 | T7 | 0.2 | Ec2 | 40 | 26.2 | 26.2 | All | 415 | 1.6 × 10$^7$ |
| 2 | T7 | 0.2 | Ec2 | 40 | 27.4 | 27.4 | All | No count | — |
| 3 | T7 | 0.2 | Ec2 | 40 | 28.6 | 28.6 | All | No count | — |
| 4 | T7 | 0.2 | Ec2 | 40 | 31 | 31 | All | No count | — |
| 5 | T7 | 0.2 | Ec2 | 40 | 33.4 | 33.4 | All | 1124 | 3.4 × 10$^7$ |
| 6 | T7 | 0.2 | Ec2 | 40 | 35.8 | 35.8 | All | 1936 | 5.4 × 10$^7$ |
| 6 | T7 | 0.2 | Ec2 | 40 | 27.50 | 27.50 | All | 1208 | 4.4 × 10$^7$ |
| 7 | T7 | 0.2 | Ec2 | 40 | 29.40 | 29.40 | All | | Not good |
| 8 | T7 | 0.2 | Ec2 | 40 | 31.20 | 31.20 | All | 1692 | 5.4 × 10$^7$ |
| 9 | T7 | 0.2 | Ec2 | 40 | 33.10 | 33.10 | All | 1392 | 4.2 × 10$^7$ |
| 10 | T7 | 0.2 | Ec2 | 40 | 34.90 | 34.90 | All | | Not good |
| 11 | T7 | 0.2 | Ec2 | 40 | 36.80 | 36.80 | All | | Not good |
| 12 | T7 | 0.2 | Ec2 | 40 | 38.60 | 38.60 | All | 3068 | 7.9 × 10$^7$ | a 1000 ml flash. The cells are inoculated with 3/500 volume of a fresh culture LB medium overnight until they reach early exponential growth phase (A600=0.4). It normally takes about 4 h to 5 h to reach the early exponential growth phase. After incubation, the cultured cells are chilled for 20 min in ice-water/on ice with frequent swirling. The cells are then harvested by centrifugation at 800 g, 4° C. for 20 min. The supernatant is discarded and the collected pellet is re-suspended gently with 250 ml of ice-cold 10% glycerol. The mixture is centrifuged again. The addition of glycerol and centrifugation are repeated for two more times. After that, the cells are re-suspended with 1 ml cold 10% glycerol. This suspension may be used immediately for electroporation or frozen in aliquots (40 µl/tube) and stored at −80° C. before use.

Electroporation

If the electrocompetent cells are stored at −80° C., the cells are thawed on ice for 10 min before electroporation. 1 µl of the plasmid DNA (1 pg to 100 ng) is added to the cells by moving the pipette through the cells while dispensing and let it sit on ice for 1-5 min. The mixture of cells and plasmid DNAs are transferred to the bottom of cold 0.2 cm electroporation cuvette. Bubbles should be avoided during the transfer. BIO-RAD MicroPulser is applied and is set to "Ec2": 0.2 cm, 2.5 kV, 6.1 ms. Pulse is applied to the mixture of cells and plasmid DNAs according to the settings. Accordingly, a pulse of 12.5 kV/cm with a time constant of 4.5-5 ms is applied to the mixture. After that, 960 µl of Super Optimal Broth (SOC) medium at 4° C. is added to the cuvette and the mixture is gently but quickly mixed with a pipette. The cells suspension is then transferred from the cuvette to a 10 ml snap-cap tube and incubated at 30° C. for 1 h with agitation at 250 rpm. Lastly, the diluted aliquots or all of the incubated suspension are spread on pre-warmed selective plates, preferably about 100 µl per plate.

It is found that 1 ng of the plasmid DNAs is the best amount to be electroporated into T7 cells based on electroporation efficiency and colonies number. Although the DNA recovery rate after precipitation by NaAc-EtOH method is low, the electroporation efficiency is acceptable ($10^7$ cfu; $1\sim2\times10^4$ colonies) when 1 ng of plasmid is transformed into the E. Coli cells.

In another example where the ligation reaction is used directly without precipitation, there is no need to heat-activate or purify the reaction mixture. However, the reaction mixture should be diluted by 100-fold to 30-60 pg DNA/µl.

IPTG Induction

In order to determine if the plasmids are successfully transformed into the E. Coli cells, the incubated suspension of the electroporation product is spread on antibiotic selection plate and incubated 24 h at 30° C. Some colonies are then selected for DNA extraction and purification such as MiniPrep to confirm the transformation. In particular, a number of colonies are randomly picked up from plate and proceeded with PCR amplification. The colonies which show sdAb insertion are proceeded with further IPTG induction and FACS analysis.

To investigate the protein expression of the recombinant cells, a single colony is selected and re-suspended in 10 ml of a liquid medium with an antibiotic. The suspension is then incubated at 37° C. until $OD_{600}$ reaches 0.4-0.8. A control reference is set at the same time. An appropriate inducer such as 10 µl of a 100 mM stock of isopropyl β-D-1-thiogalactopyranoside (IPTG) is added into the suspension. The mixture is incubated at 37° C. for 2 h. After IPTG induction, the cells are either lysed for protein expression determination or subject to flow cytometry analysis.

There are two sets of conditions for IPTG inductions, as shown in Table 6 and 7 below. The later flow cytometry analysis shows that the IPTG induction carried at 37° C. produces better protein expression than that at 25° C. In particular, the peaks of PE-A population at 37° C. shows a stronger shift than that at 25° C. 0.1 mM of the inducer at 37° C. for 2 h gives the best results, as about 40% of the population has protein expression. Accordingly, it is suggested using the IPTG conditions as: starting at OD600=0.5; 0.1 mM of IPTG, 37° C., and for 2 h.

TABLE 6

First set of optimal IPTG induction conditions.

| | #1 | #2 | #3 | #4 | #5 |
|---|---|---|---|---|---|
| 37° C., 2 h | Control 1 ml | 0.001 mM 1 ml | 0.01 mM 1 ml | 0.1 mM 1 ml | 0.4 mM 1 ml |

TABLE 5

The transformation efficiency obtained after electroporation. #1-4 are results of transforming plasmids obtained by NaAc-EtOH DNA precipitation method. #5-7 are results of transforming plasmids obtained by MiniPrep.

| # | Strain (cm) | Cuvette (cm) | Model | Bacterial vol. (µl) | DNA conc. (ng/µl) | DNA quantity used (ng) | Dilution folds before plating (100 µl for plating) | Colonies in one plate (only one plate per group) | Transformation efficiency (cfu/µg DNA) |
|---|---|---|---|---|---|---|---|---|---|
| 1 | T7 | 0.2 | Ec2 | 40 | 0.05 | 0.05 | All | 37 | $7.4 \times 10^5$ |
| 2 | T7 | 0.2 | Ec2 | 40 | 0.5 | 0.5 | All | ~3000 | $6 \times 10^6$ |
| 3 | T7 | 0.2 | Ec2 | 40 | 1 | 1 | All | Too many | Maybe $2 \times 10^7$ cfu; $\sim1\text{-}2 \times 10^4$ colonies |
| 4 | T7 | 0.2 | Ec2 | 40 | 10 | 10 | 20 | 1463 | $3.0 \times 10^6$ cfu; $\sim2.8 \times 10^4$ colonies |
| 5 | T7 | 0.2 | Ec2 | 40 | 1 | 1 | 2000-fold | 316 | $6.3 \times 10^8$ cfu; $\sim6.3 \times 10^5$ colonies |
| 6 | T7 | 0.2 | Ec2 | 40 | 10 | 10 | 2000-fold | 560 | $1.1 \times 10^8$ |
| 7 | T7 | 0.2 | Ec2 | 40 | 100 | 100 | 2000-fold | 730 | $1.5 \times 10^7$ |

TABLE 6-continued

First set of optimal IPTG induction conditions.

| | #6 | #7 | #8 | #9 | #10 |
|---|---|---|---|---|---|
| 25° C., Overnight 20 h | Control 1.5 ml | 0.001 mM 1.5 ml | 0.01 mM 1.5 ml | 0.1 mM 1.5 ml | 0.4 mM 1.5 ml |
| | #11 | #12 | #13 | #14 | #15 |
| 16° C. Overnight 20 h | Control 1.5 ml | 0.001 mM 1.5 ml | 0.01 mM 1.5 ml | 0.1 mM 1.5 ml | 0.4 mM 1.5 ml |

TABLE 7

Second set of optimal IPTG induction conditions.

| | #1 | #2 | #3 | #4 | #5 | #6 |
|---|---|---|---|---|---|---|
| 37° C., 2 h | Control 0.1% | 0.1 mM 39.7% | 0.2 mM 39.6% | 0.4 mM 36% | 0.8 mM 28.1% | 1 mM 34.4% |
| | #7 | #8 | #9 | #10 | #11 | #12 |
| 25° C., Overnight 16 h | Control 0.4% | 0.1 mM 20.7% | 0.2 mM 16.1% | 0.4 mM 17.2% | 0.8 mM 17.4% | 1 mM 15.4% |

Determination of Protein Expression

The protein expression is determined by using Coomassie stained protein gel, Western blot analysis or activity assay. The protein expression in both the total cell extract (soluble+insoluble) is determined, as well as in the soluble fraction alone.

Before carrying out SDS-PAGE gel electrophoresis and Western blot analysis, the induced cells are collected for cell lysis. The harvested cells are subject to centrifugation at 12,000 rpm for 1 min, to form supernatant and cell residue. The supernatant is discarded and the residue is frozen as pellet at −70° C. Next, 1 ml of OD600 1.5 of bacterial cell culture is re-suspended in 80 μl of 10 mM Tris HCl (pH 8.0), and mixed with 20 μl of SDS-Urea buffer (5×). The mixture is boiled for 5 min. The final concentration of urea is 4M. The boiled samples are subject to centrifugation at 14,000 g for 5 min to settle the insoluble material. The resultant products are loaded onto a 10% SDS-PAGE gel. The method of staining proteins in gels with Coomassie is performed as described in Lawrence A. et al., J. Vis. Exp. (30), 2009.

Figure 12:
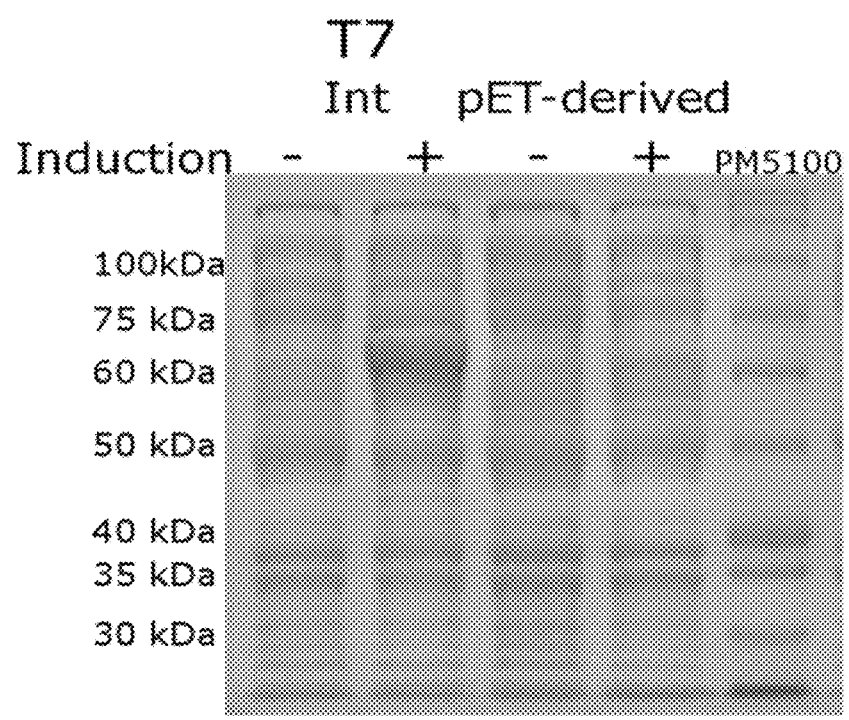
FIG. 12 shows the expression of intimin in recombinant E. Coli cells based on the staining of proteins in SDS-PAGE gels with Coomassie G-250.

FIG. 12 shows the expression of intimin in recombinant E. Coli cells based on the staining of proteins in SDS-PAGE gels with Coomassie G-250.

For Western blot analysis, 10 μl of sample-SDS loading dye is loaded into wells of 10% SDS-PAGE gel, along with molecular weight marker. The gel is then run for 50 min at 150V. After transferring into a PVDF membrane, the PVDF membrane is blocked with 5% milk TBST for 1 h at room temperature. Subsequently, the membrane is incubated with anti-horn shark IgNar antibody (1:3000, 5% milk with TBST, 1:1250 of 25% sodium azide) for 1 h at 37° C. The membrane is then washed with TBST repeatedly and further incubated with anti-rabbit IgG-HRP conjugated antibody (1:2000, 5% milk with TBST) for 1 h at 37° C. After the secondary incubation, the membrane is washed again with TBST repeatedly. Lastly, the protein expression can be detected by use of ECL chemiluminescence system. Preferably, the membrane may be stained before detection. In another example, the first incubation uses anti-c-Myc antibody (1:50) for overnight at 4° C.; and the second incubation uses anti-Mouse IgG-HRP conjugated antibody (1:3000) for 1 h at 37° C.

Figure 13:
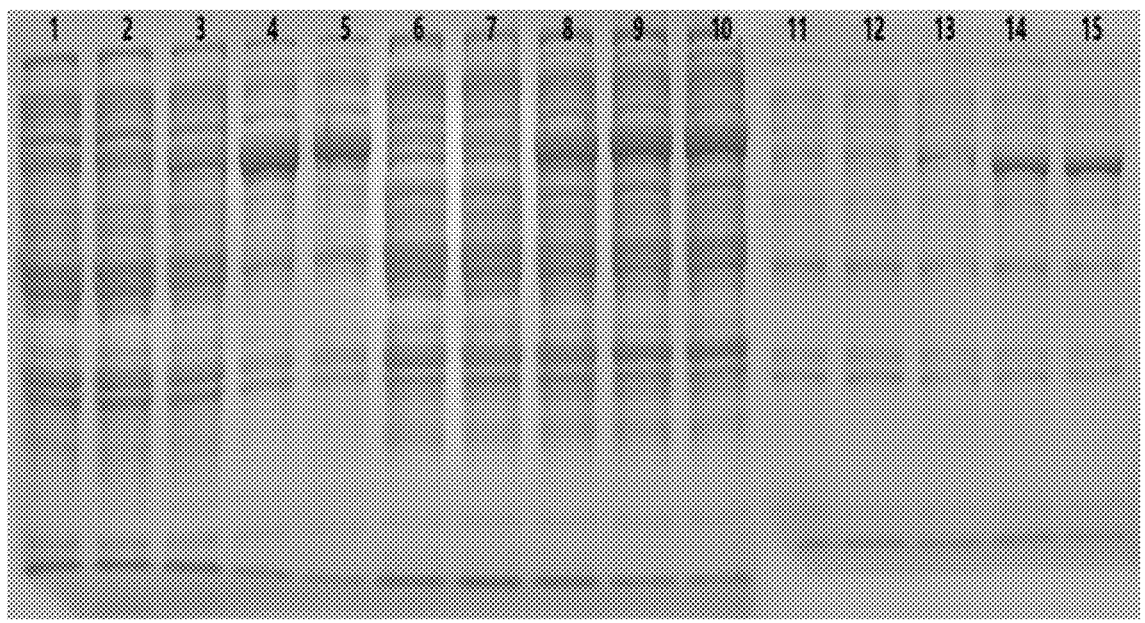
FIG. 13 shows the protein expression at different IPTG induction conditions corresponding to the first experimental design, via Western blot analysis.
Figure 14:
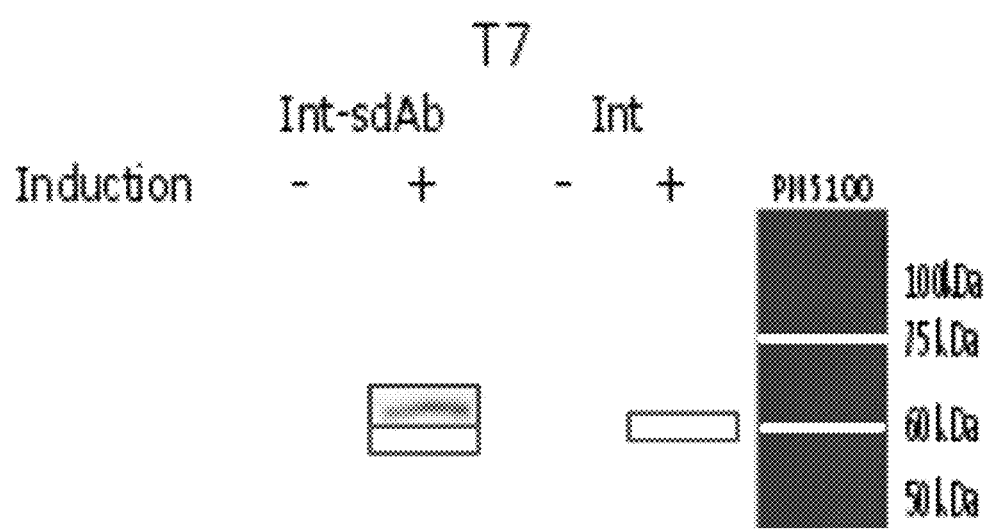
FIG. 14 shows that intimin-sdAb can be expressed in the recombinant E. Coli cells.
Figure 15:
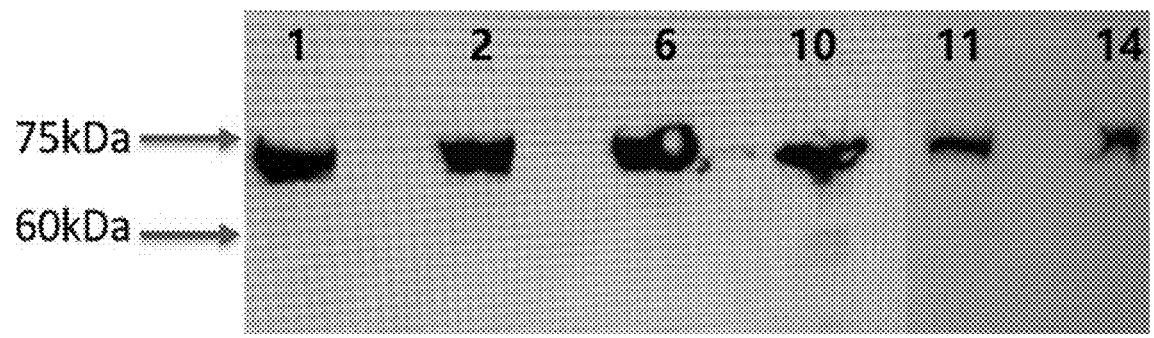
FIG. 15 shows that 6 colonies of recombinant E. Coli cells express intimin-sdAb, the expression are shown as about 75 kDa which is closed to the expected size of intimin-sdAb.

For instance, FIG. 13 shows the protein expression at different IPTG induction conditions corresponding to the first experimental design, via Western blot analysis. FIG. 14 shows that intimin-sdAb can be expressed in the recombinant E. Coli cells. FIG. 15 shows that 6 colonies of recombinant E. Coli cells express intimin-sdAb, the expression are shown as about 75 kDa which is closed to the expect size of intimin-sdAb. The first incubation is conducted by use of anti-horn shark IgNar Ab (1:3000) for 1 h at 37° C., and the second incubation is conducted with anti-rabbit IgG-HRP conjugated Ab (1:2000) for 1 h at 37° C.

Flow Cytometry Analysis

Fluorescent activated cell sorting is used to screen out target sequences of IgNAR which specifically against antigens. Sorted bacteria were sent out for sequencing.

For standard flow cytometry analysis, induced recombinant cells (1.5 ml, OD600 of 1.0) are harvested by centrifugation at 2,300 g for 5 min. The collected cells are washed with 1 ml of PBS (which is filter-sterilized) and re-suspended with PBS to form a suspension having a final volume of 200 μl. Next, the suspension is incubated with GFP (final concentration of 0.06 mg/ml) or antibody (e.g. PE-Myc Mouse 9611, diluted 200×) for 30 min at 30° C. in the dark. After incubation, the cells are washed twice with 1 ml of PBS, and re-suspended in 250 μl of PBS. For each experiment, at least 100,000 cells are analyzed in a cytometer (Gallios, Beckman Coulter).

Figure 16:
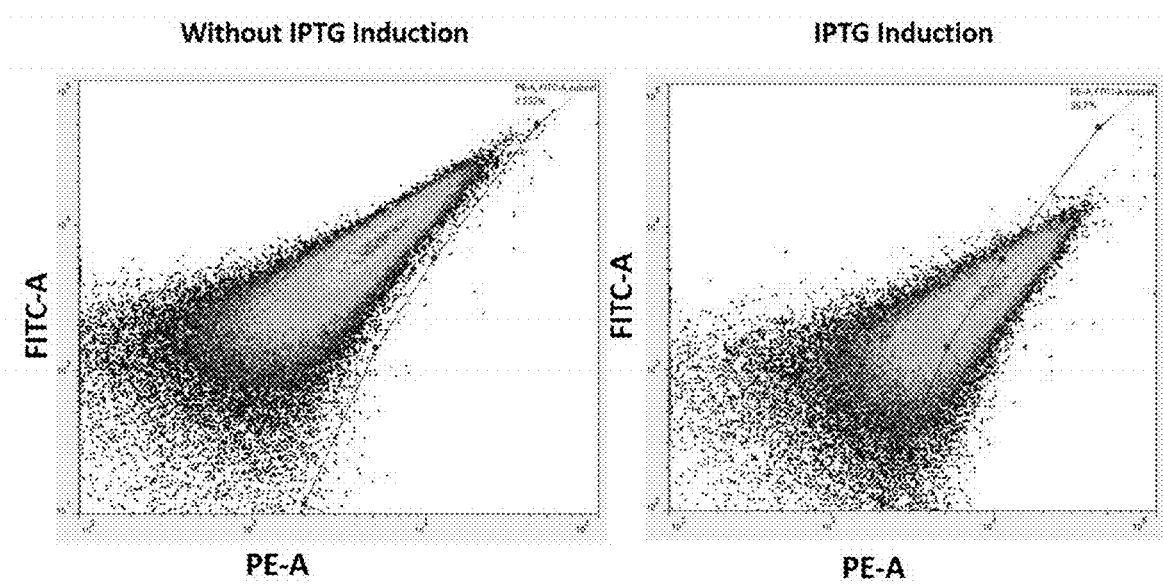
FIG. 16 shows the patterns obtained from flow cytometry analysis, in which the living cells were stained with fluorescent PE-myc antibody (9B11).
Figure 17A:
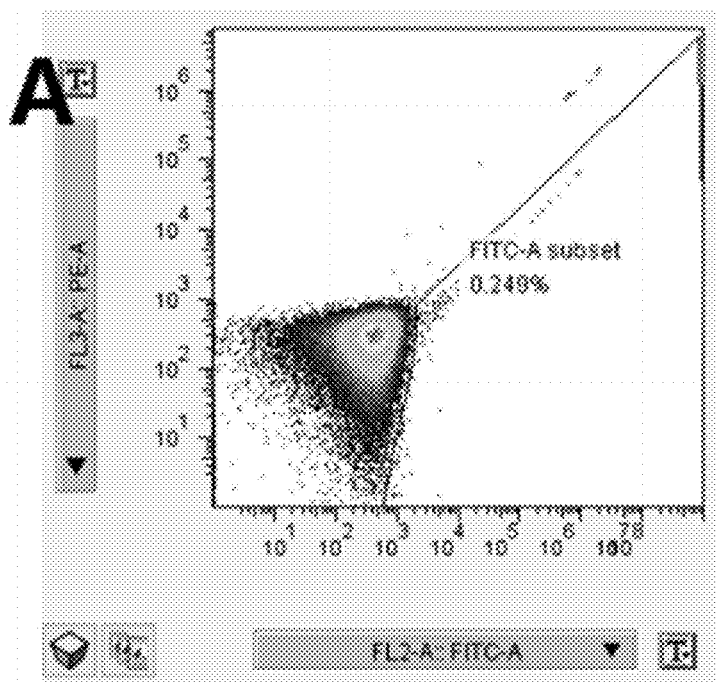
FIGS. 17A through 17F show the expression of E. Coli after IPTG induction and GFP staining, in particular the cells producing GFP-positive sdAbs are gated according negative control and screened out by FACS.
Figure 17B:
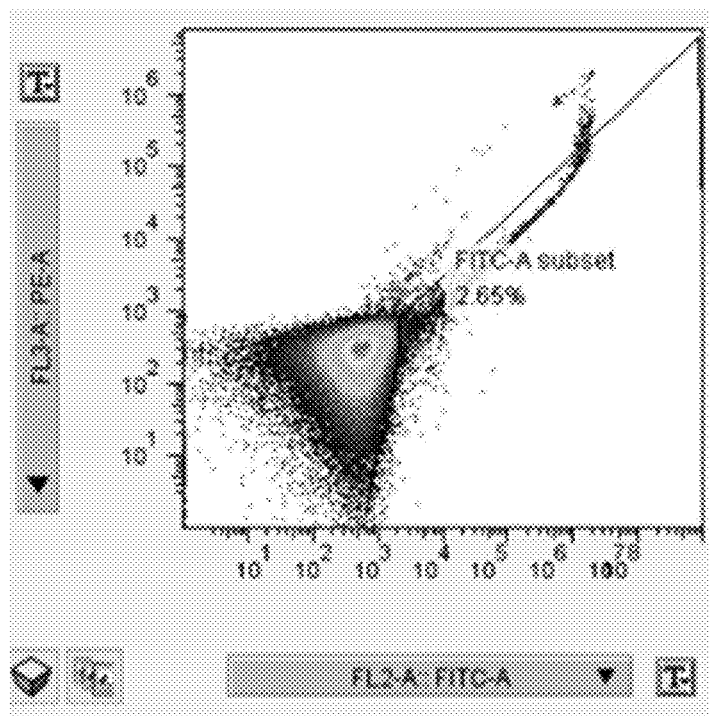
Figure 17C:
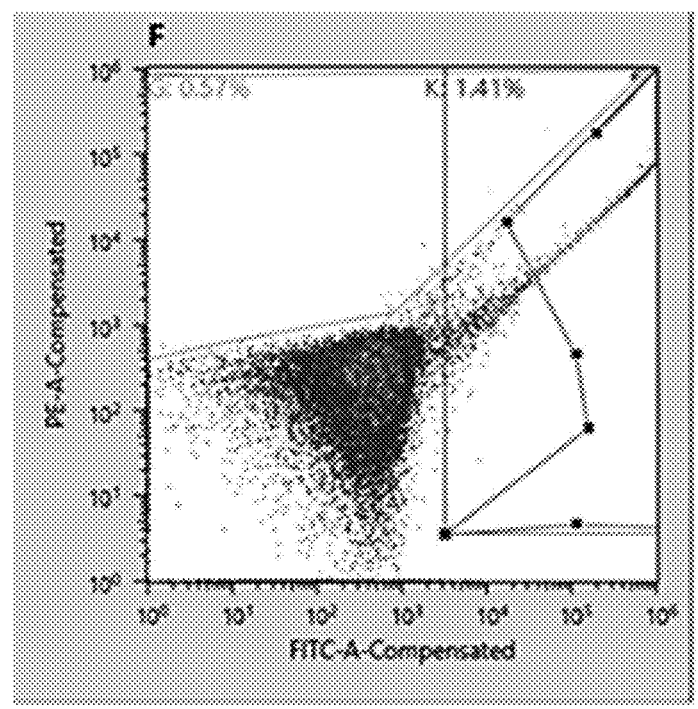
Figure 17D:
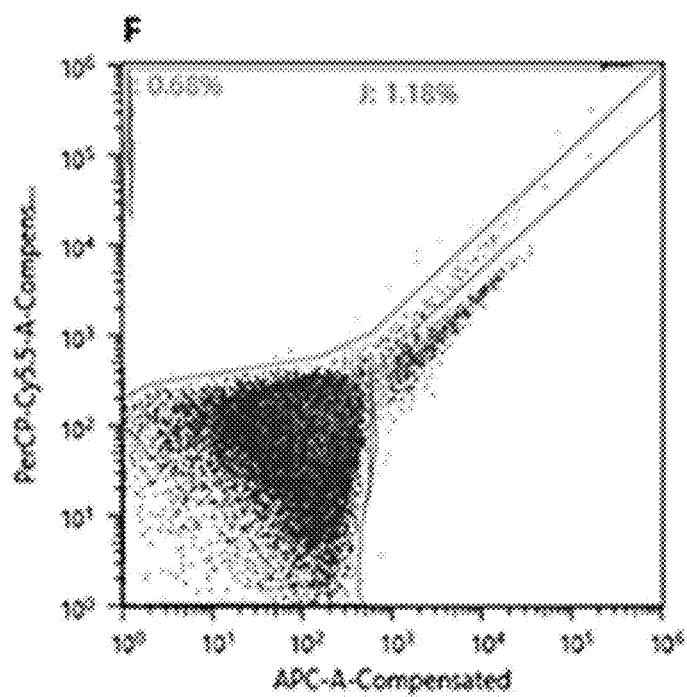
Figure 17E:
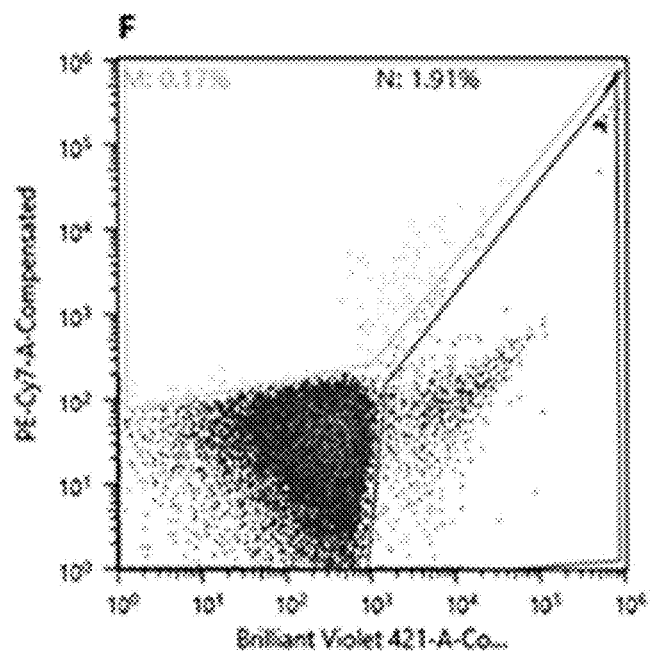
Figure 17F:
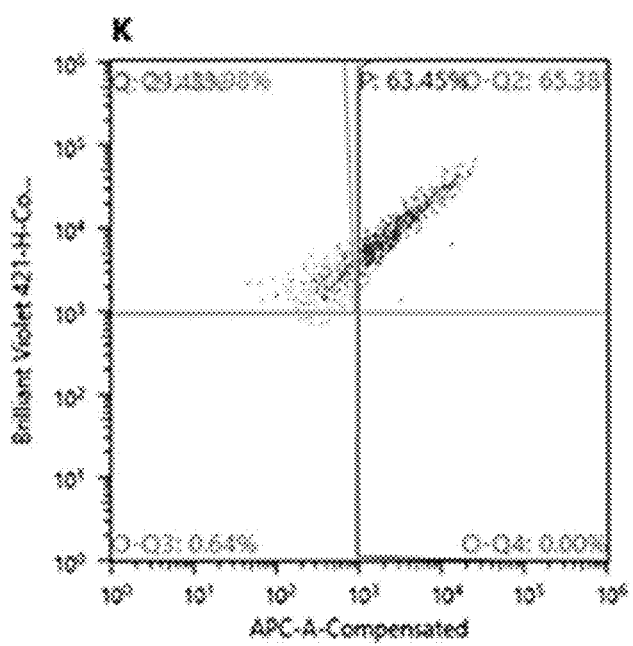

FIG. 16 shows the patterns obtained from flow cytometry analysis, in which the living cells were stained with fluorescent PE-myc antibody (9611). In particular, it demonstrates that intimin-sdAb can be expressed on the outer membrane of E. Coli.

FIG. 17 shows the expression of E. Coli after IPTG induction and GFP staining. Besides, the populations with APC and Brilliant-Violet-421 signals are also screened out for further selection. FIG. 17A shows the positive population on FITC signal, in the first round, of screening by FACS. FIGS. 17B, C, D, E and F come from the same sample used in FIG. 17A, in particular same ancestor population, and show the result in the third round of screening by FACS. The population level in FIGS. 17B, C, D and E are the same. FIG. 17F shows the child population of FITC-positive population in FIG. 17C and shows the positive population on both of APC and Brilliant Violet 421 signals, which indicates the spectral shift of GFP after its binding to sdAbs. FIG. 17A and FIG. 17B are generated by FlowJo software, while others are generated by Sony SH800 software.

Figure 18:
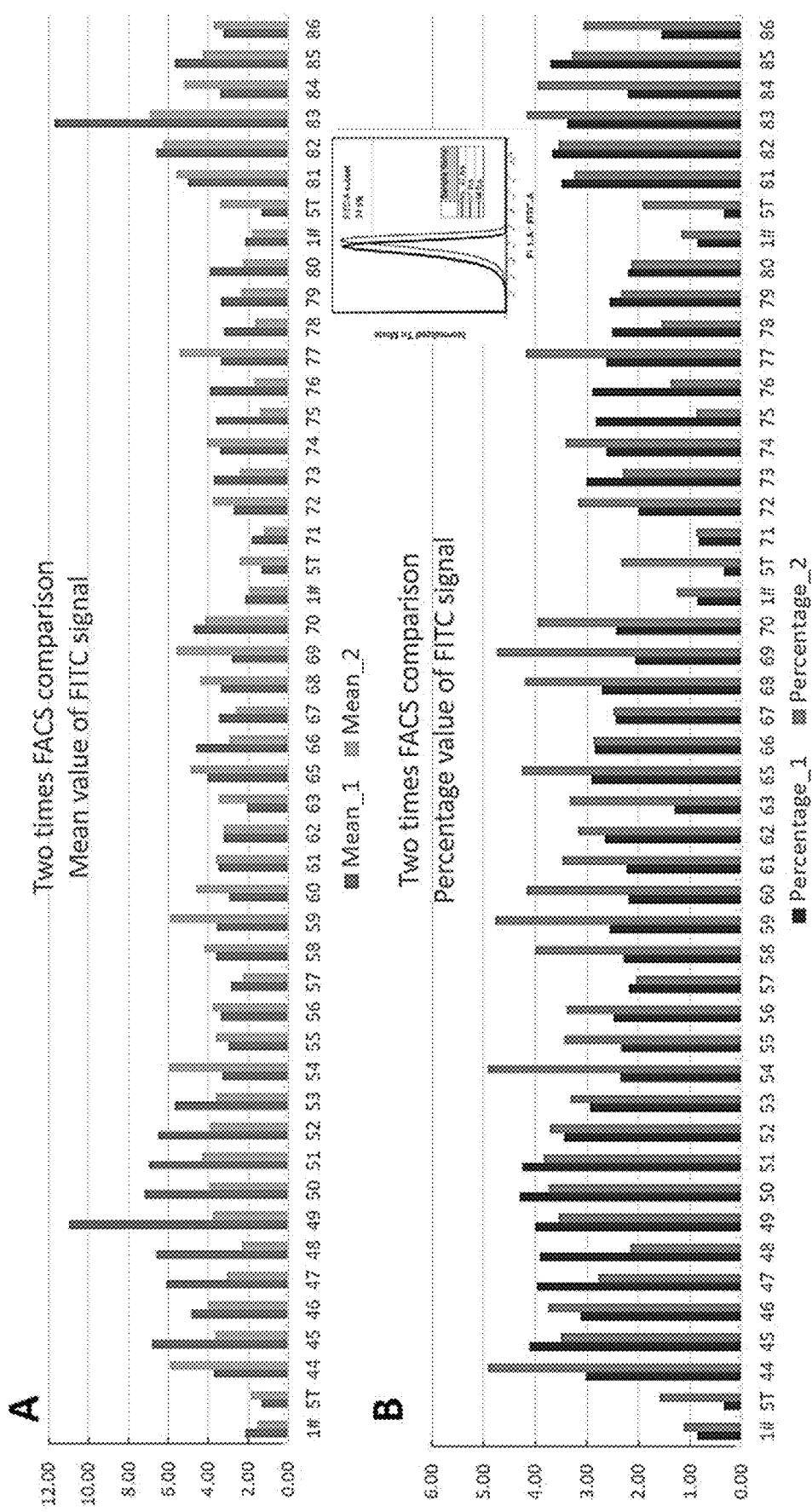
FIG. 18 shows the two times FACS comparison of mean value and percentage value of FITC signal of different strains with sdAb expression.

FIG. 18 shows the two times FACS comparison of mean value and percentage value of FITC signal of different strains with sdAb expression. According to the results, the top 10 GFP-positive strains on FITC signal performance are No. 44, 46, 50, 51, 52, 53, 65, 70, 82, and 83 as recorded in the sequence listing as SEQ ID NO: 10-20.

Mass Production

The selected E Coli cells can be applied in mass production of the identified sdAbs. In particular, the incubated recombinant cells may be induced with IPTG, and collected by centrifugation. The cells pellets are then re-suspended in lysis buffer and the IgNARs are purified by fast protein liquid chromatography. Accordingly, the purified sdAbs may be applied in various applications.

The invention claimed is:

1. A method of producing an antibody fragment for a target antigen comprising steps of:
   a) administering an immunizing mixture containing the target antigen to a bamboo shark from the genus of *Chiloscyllium* for at least two times;
   b) collecting a blood sample from the bamboo shark;
   c) extracting RNAs from the blood sample;
   d) subjecting said RNAs to reverse transcription to obtain a complementary DNA, and amplifying the cDNA to obtain a mixture of amplified cDNAs followed by purification, wherein the cDNA is amplified by using at least one primer set selected from the group consisting of a set of SEQ ID NO: 3 and SEQ ID NO: 4, and a set of SEQ ID NO: 7 and SEQ ID NO: 8;
   e) inserting the cDNA obtained in step d) into a vector to produce a recombinant plasmid;
   f) purifying the recombinant plasmid by precipitation using an alcohol and a salt; and introducing the recombinant plasmid into a bacterial cell to form a recombinant cell; and
   g) incubating the recombinant cell and extracting the antibody fragment from the incubated recombinant cell.

2. The method of claim 1, wherein the bamboo shark is *Chiloscyllium punctatum*.

3. The method of claim 1, wherein the immunizing mixture comprises the target antigen and a Freund's Adjuvant.

4. The method of claim 1, wherein in the step a), the bamboo shark is administered with the immunizing mixture once per month and for at least 3 months.

5. The method of claim 1, wherein the antibody fragment is a single domain antibody.

6. The method of claim 1, wherein the recombinant plasmid comprises an intimin domain.

7. The method of claim 1, wherein in the step e), the molar ratio of the cDNA to the vector is in a range of about 5:1 to about 9:1.

8. The method of claim 1, wherein the bacterial cell is an *E. coli* cell.

9. The method of claim 1, wherein the target antigen is a fluorescent molecule or an organic dye.

10. A method of producing an antibody fragment for a target antigen from a bamboo shark from the genus of *Chiloscyllium*, comprising steps of:
    a) administering an immunizing mixture containing the target antigen to the shark for at least two times, wherein the target antigen is a fluorescent molecule or an organic dye;
    b) collecting a blood sample from the bamboo shark; and
    c) extracting RNAs from the blood sample; and
    d) subjecting said RNAs to reverse transcription to obtain a complementary DNA, and amplifying the cDNA to obtain a mixture of amplified cDNAs followed by purification, wherein the cDNA is amplified by using at least one primer set selected from the group consisting of a set of SEQ ID NO: 3 and SEQ ID NO: 4, and a set of SEQ ID NO: 7 and SEQ ID NO: 8.

11. The method of claim 10, wherein the bamboo shark is *Chiloscyllium punctatum*.

12. The method of claim 10, wherein the immunizing mixture is administered to the bamboo shark once per month for at least three times.

13. The method of claim 10, wherein the immunizing mixture comprises the target antigen and a Freund's Adjuvant.

14. The method of claim 10, wherein the target antigen is green fluorescent protein.

15. The method of claim 10, further comprising a step of inserting the cDNA to a vector to form a recombinant plasmid, wherein the vector comprises an intimin domain; and introducing the recombinant plasmid to an *E. coli* cell to form a recombinant cell.

16. The method of claim 15, further comprising a step of incubating the recombinant cell and extracting the antibody fragment.

17. The method of claim 10, wherein the antibody fragment is a single domain antibody.

18. A method of determining the presence or the amount or both the presence and the amount of a target antigen in a sample for detection, comprising steps of:
    practicing the method of claim 1;
    adding the extracted antibody fragment into the sample for detection, and incubating the mixture for a period of time; and
    performing quantitative or qualitative analysis to determine the presence or the amount or both the presence and the amount of the target antigen in the mixture.

19. The method of claim 18, wherein the sample is a biological sample obtained from a patient.

* * * * *

SEQUENCE LISTING

```
<160> NUMBER OF SEQ ID NOS: 19

<210> SEQ ID NO 1
<211> LENGTH: 22
<212> TYPE: DNA
<213> ORGANISM: Artificial Sequence
<220> FEATURE:
<223> OTHER INFORMATION: Synthesized

<400> SEQUENCE: 1
gggtagacca aacaccaaga ac                                              22

<210> SEQ ID NO 2
<211> LENGTH: 23
<212> TYPE: DNA
<213> ORGANISM: Artificial Sequence
<220> FEATURE:
<223> OTHER INFORMATION: Synthesized

<400> SEQUENCE: 2
gaggagactg actattggtg gag                                             23

<210> SEQ ID NO 3
<211> LENGTH: 25
<212> TYPE: DNA
<213> ORGANISM: Artificial Sequence
<220> FEATURE:
<223> OTHER INFORMATION: Synthesized

<400> SEQUENCE: 3
aaaagagacg gacgaatcac tgacc                                           25

<210> SEQ ID NO 4
<211> LENGTH: 16
<212> TYPE: DNA
<213> ORGANISM: Artificial Sequence
<220> FEATURE:
<223> OTHER INFORMATION: Synthesized

<400> SEQUENCE: 4
cggtcagtcc ggtgcc                                                     16

<210> SEQ ID NO 5
<211> LENGTH: 21
<212> TYPE: DNA
<213> ORGANISM: Artificial Sequence
<220> FEATURE:
<223> OTHER INFORMATION: Synthesized

<400> SEQUENCE: 5
wttcacagtc asarkggtsc c                                               21

<210> SEQ ID NO 6
<211> LENGTH: 25
<212> TYPE: DNA
<213> ORGANISM: Artificial Sequence
<220> FEATURE:
<223> OTHER INFORMATION: Synthesized

<400> SEQUENCE: 6
atggccsmac ggsttgaaca aacac                                           25

<210> SEQ ID NO 7
<211> LENGTH: 33
<212> TYPE: DNA
<213> ORGANISM: Artificial Sequence
```

<220> FEATURE:
<223> OTHER INFORMATION: Synthesized

<400> SEQUENCE: 7
gggaagcttg ccgcacgggt tgaacaaaca ccg          33

<210> SEQ ID NO 8
<211> LENGTH: 33
<212> TYPE: DNA
<213> ORGANISM: Artificial Sequence
<220> FEATURE:
<223> OTHER INFORMATION: Synthesized

<400> SEQUENCE: 8
ggcgaattcc acagtcagag gggtgccgcc tcc          33

<210> SEQ ID NO 9
<211> LENGTH: 1677
<212> TYPE: DNA
<213> ORGANISM: Artificial Sequence
<220> FEATURE:
<223> OTHER INFORMATION: Synthesized

<400> SEQUENCE: 9

| | |
|---|---|
| atgattactc atggttgtta tacccggacc cggcacaagc ataagctaaa aaaaacattg | 60 |
| attatgctta gtgctggttt aggattgttt ttttatgtta atcagaactc atttgcaaat | 120 |
| ggtgaaaatt attttaaatt gggttcggat tcaaaactgt taactcatga tagctatcag | 180 |
| aatcgccttt tttatacgtt gaaaactggt gaaactgttg ccgatctttc taaatcgcaa | 240 |
| gatattaatt tatcgacgat ttggtcgttg aataagcatt tatacagttc tgaaagcgaa | 300 |
| atgatgaagg ccgcgcctgg tcagcagatc attttgccac tcaaaaaact tccctttgaa | 360 |
| tacagtgcac taccactttt aggttcggca cctcttgttg ctgcaggtgg tgttgctggt | 420 |
| cacacgaata aactgactaa aatgtccccg gacgtgacca aaagcaacat gaccgatgac | 480 |
| aaggcattaa attatgcggc acaacaggcg gcgagtctcg gtagccagct tcagtcgcga | 540 |
| tctctgaacg gcgattacgc gaaagatacc gctcttggta cgctggtaa ccaggcttcg | 600 |
| tcacagttgc aggcctggtt acaacattat ggaacggcag aggttaatct gcagagtggt | 660 |
| gataactttg acggtagttc actggacttc ttattaccgt tctatgattc gaaaaaatg | 720 |
| ctggcatttg gtcaggtcgg agcgcgttac attgactccc gctttacggc aaatttaggt | 780 |
| gcgggtcagc gttttttcct tcctgcaaac atgttgggct ataacgtctt cattgatcag | 840 |
| gattttctg tgataatac ccgtttaggt attggtggcg aatactggcg agactatttc | 900 |
| aaaagtagcg ttaacggcta tttccgcatg aggcgctggc atgagtcata ccataagaaa | 960 |
| gactatgatg agcgcccagc aaatggcttc gatatccgtt taatggcta tctaccgtca | 1020 |
| tatccggcat taggcgccaa gctgatatat gagcagtatt atggtgataa tgttgctttg | 1080 |
| tttaattctg ataagctgca gtcgaatcct ggtgcggcga ccgttggtgt aaactatact | 1140 |
| ccgattcctc tggtgacgat ggggatcgat taccgtcatg gtacgggtaa tgaaaatgat | 1200 |
| ctccttact caatgcagtt ccgttatcag tttgataaat cgtggtctca gcaaattgaa | 1260 |
| ccacagtatg ttaacgagtt aagaacatta tcaggcagcc gttacgatct ggttcagcgt | 1320 |
| aataacaata ttattctgga gtacaagaag caggatattc tttctctgaa tattccgcat | 1380 |
| gatattaatg gtactgaaca cagtacgcag aagattcagt gatcgttaa gagcaaatac | 1440 |
| ggtctggatc gtatcgtctg ggatgatagt gcattacgca gtcagggcgg tcagattcag | 1500 |

```
catagcggaa gccaaagcgc acaagactac caggctattt tgcctgctta tgtgcaaggt    1560
ggcagcaata tttataaagt gacggctcgc gcctatgacc gtaatggcaa tagctctaac    1620
aatgtacagc ttactattac cgttctgtcg aatggtcaag ttgtcgacca ggtttggg      1677
```

<210> SEQ ID NO 10
<211> LENGTH: 336
<212> TYPE: DNA
<213> ORGANISM: Artificial Sequence
<220> FEATURE:
<223> OTHER INFORMATION: Synthesized

<400> SEQUENCE: 10

```
aagcttgccg cacgggttga acaaacaccg acaacgacga caaaggagac aggcgaatca     60
ctgaccatca attgcgtcct aaaaggttcc agctatgcat tgtgtgacac gtcatggtat    120
ttcacaaaaa agggcgcaac aaagaaggag gttttatcaa atggcggacg atacgcggaa    180
acagttcaca aggcatcaaa gtccttttct ttgcgaatta gtgacctaag agttgaagac    240
agtggtacat atcactgtaa aggctataga ggaacctatc actgcccgag gtatgactat    300
tatgaaggag gcggcacccc tctgactgtg gaattc                              336
```

<210> SEQ ID NO 11
<211> LENGTH: 342
<212> TYPE: DNA
<213> ORGANISM: Artificial Sequence
<220> FEATURE:
<223> OTHER INFORMATION: Synthesized

<400> SEQUENCE: 11

```
aagcttgccg cacgggttga acaaacaccg acaacgacaa caaaggaggc aggcgaatca     60
ctgaccatca attgcgtcct aaaaggttcc agttatgcat tgtgtgacac gtcttggtat    120
tttacaaaaa aagacgcaac aaagaaggag aacttatcaa atggcggacg atacgcggaa    180
acagtgaaca agacatcaaa gtccttttct ttgcgaattg gtgacctaag agctgaagac    240
agtggtatat atgtctgtaa agcgtaccgg ggagctggcc gaaactgttt tagtcgggat    300
gacttttatg aaggaggcgg cacccctctg actgtggaat tc                       342
```

<210> SEQ ID NO 12
<211> LENGTH: 342
<212> TYPE: DNA
<213> ORGANISM: Artificial Sequence
<220> FEATURE:
<223> OTHER INFORMATION: Synthesized

<400> SEQUENCE: 12

```
aagcttgccg cacgggttga acaaacaccg acaacgacaa caaaggaggc aggcgaatca     60
ctgaccatca attgcgtcct aaaaggttcc agctatgcat tgtgtaacac gtactggtat    120
ttcacaaaaa agggcgctac aaagaaggag agcttatcaa atggcggacg atacgcggaa    180
acagtgaaca aggcatcaaa gtccttttct ttgcgaatta gtgacctaag agttgaagac    240
agtggtacat atcactgtaa agcgttcccc cagctggatg aggtttctta gctggaggga    300
tccccatatg aaggaggcgg cacccctctg actgtggaat tc                       342
```

<210> SEQ ID NO 13
<211> LENGTH: 351
<212> TYPE: DNA
<213> ORGANISM: Artificial Sequence
<220> FEATURE:
<223> OTHER INFORMATION: Synthesized

<400> SEQUENCE: 13

```
aagcttgccg cacgggttga acaaacaccg acaacgacaa caaaggaggc aggcgaatca    60
ctgaccatca attgcgtcct aaaaggttcc agctatgcat tgtgtgacac gtactggtat   120
ttcacaaaaa agggcgcaac aaagaaggag agcttatcaa atggcggacg atacgcggaa   180
acagtgaaca aggcatcaaa gtcctcttct ttgcgaatta gtgacctaag agttgaagac   240
agtggtacat atcactgtaa agcgtcacag acggatgagg gaggttactg ttatacccat   300
aactggaact actattatga aggaggcggc acccctctga ctgtggaatt c            351
```

<210> SEQ ID NO 14
<211> LENGTH: 333
<212> TYPE: DNA
<213> ORGANISM: Artificial Sequence
<220> FEATURE:
<223> OTHER INFORMATION: Synthesized

<400> SEQUENCE: 14

```
aagcttgccg cacgggttga acaaacaccg acattgacaa caaaggaggc aggcgaatca    60
ctgaccatca attgcgtcct aaaaggttcc agcaatgtat tgtgtaacac gtactggtat   120
ttcacaaaaa agggcgcaac aaagaaggag agcttatcaa atggcggacg atacgtggag   180
acagtgaaca aggcatcaaa gtccttttct ttgcgaatca gtgacctagg agttgaagac   240
agtggtacat atcactgtaa agcggctggt tgcaaccggg tatacgtgac cggaccctat   300
gaaggaggcg gcacccctct gactgtggaa ttc                                333
```

<210> SEQ ID NO 15
<211> LENGTH: 351
<212> TYPE: DNA
<213> ORGANISM: Artificial Sequence
<220> FEATURE:
<223> OTHER INFORMATION: Synthesized

<400> SEQUENCE: 15

```
aagcttgccg cacgggttga acaaacaccg acaacgacaa caaagggcgc aggcgaatca    60
ctgaccatca attgcgtcct aaaaggttcc aactatgcag tgtgtgacac gtactggtat   120
ttcacaaaac cgggggcaac aaaaaaggag aacttatata atggcggacg atacgcggaa   180
acagtgaaca aggcatcaaa gtccttttct ttgcgaatta gtgacctaag agttgaagac   240
agtggtacat atcactgtaa agcgggctac agctggtcta ctggaacctg ggattgcccc   300
cgggcatatg actattatga aggaggcggc acccctctga ctgtggaatt c            351
```

<210> SEQ ID NO 16
<211> LENGTH: 342
<212> TYPE: DNA
<213> ORGANISM: Artificial Sequence
<220> FEATURE:
<223> OTHER INFORMATION: Synthesized

<400> SEQUENCE: 16

```
aagcttgccg cacgggttga acaaacaccg acaacgacaa caaaggaggc aggcgaatca    60
ctgaccatca attgcgtcct aaaaggttcc agatatgcat tgtgtgacac gtactgggat   120
ttcacaaaaa agggcgcaac aaagaaggag agcttatcaa atggcggacg atacgcggaa   180
acagtgaaca aggcatcaaa gtccttttct ttgcgaatta gtgacctaag agttgaagac   240
agtggtacat atcactgtaa ggcgtatttc tctagctgga gggactgtta tacagtggga   300
```

```
gactatcatg aaggaggcgg caccccctctg actgtggaat tc          342
```

<210> SEQ ID NO 17
<211> LENGTH: 339
<212> TYPE: DNA
<213> ORGANISM: Artificial Sequence
<220> FEATURE:
<223> OTHER INFORMATION: Synthesized

<400> SEQUENCE: 17

```
aagcttgccg cacgggttga acaaacaccg acaacgacaa caaaggaggc aggcgaatca    60
ctgaccatca attgcgtcct aaaaggatcc ggctatagat tgtgtaacac gtactggtat   120
ttcacaaaag agggccttac aaagaaggag agcctatcaa atggcggacg atacgcggaa   180
acaatgaaca aggcgtcaaa gtcctttttct ttgcgaatta gtgacctaag agttgaagac   240
agtggcacat atcactgtaa aacggaagac agcgaagatg gatgttatac gcccccgcga   300
gattatgaag gaggcggcac ccctctgact gtggaattc                           339
```

<210> SEQ ID NO 18
<211> LENGTH: 351
<212> TYPE: DNA
<213> ORGANISM: Artificial Sequence
<220> FEATURE:
<223> OTHER INFORMATION: Synthesized

<400> SEQUENCE: 18

```
aagcttgccg cacgggttga acaaacaccg acaacgacaa caaaggaggc aggcgaatca    60
ctgaccatca attgcgtcct aaaaggttct agttatgtat tgtgtaacac gtactggtat   120
ttcacaaaaa agggcgctac aaagaaggag agcttatgaa atggcggacg atacgcggaa   180
acagtgaaca aggcatcaaa gtcctttttct ttgcgaatta gtgacctaag agttgaagac   240
agtggtacac atctcagtga aagcgtgcag ctggaagaat cgactgttat acgggctgga   300
aggaccgggt actattatgg aggaggcggc acccctctga ctgtggaatt c             351
```

<210> SEQ ID NO 19
<211> LENGTH: 327
<212> TYPE: DNA
<213> ORGANISM: Artificial Sequence
<220> FEATURE:
<223> OTHER INFORMATION: Synthesized

<400> SEQUENCE: 19

```
aagcttgccg cacgggttga acaaacaccg acaacgacaa caaaggaggc aggcgaatca    60
ctgaccatca attgcgtcct aaaaggttcc agcaatgtat tgtgtaacac atactggtat   120
ttcacaaaaa agggcgccac gaagaaggag agcttatcaa atggcggacg atacgcggaa   180
acagtgaaca aggcatcaaa gtcctttttct ttgcgaatta gtgacctaag agttgaagac   240
agtggtacat atcactgtaa agcgtctggt aagggctgtt atgatggtca ttatgaagga   300
ggcggcaccc ctctgactgt ggaattc                                         327
```